United States Patent
Roe et al.

[11] Patent Number: 6,093,869
[45] Date of Patent: *Jul. 25, 2000

[54] DISPOSABLE ARTICLE HAVING A RESPONSIVE SYSTEM INCLUDING A FEEDBACK CONTROL LOOP

[75] Inventors: Donald C. Roe, West Chester; Patrick J. Allen, Cincinnati, both of Ohio; Bruno J. Ehrnsperger, Frankfurt am Main; Mattias Schmidt, Idstein, both of Germany; Karl P. Ronn, Cincinnati, Ohio; Mikhail K. Kruchinin, St. Petersburg, Russian Federation; Simon S. Litvin, Brighhton, Mass.; Oleg N. Khomjakov, Saint Petersburg, Russian Federation

[73] Assignee: The Procter & Gamble Company, Cincinnati, Ohio

[*] Notice: This patent is subject to a terminal disclaimer.

[21] Appl. No.: 09/107,563

[22] Filed: Jun. 29, 1998

[51] Int. Cl.⁷ .................................... A61F 13/15
[52] U.S. Cl. ......................... 604/361; 604/358; 604/359; 604/360; 604/362; 604/367; 604/378; 604/385.01; 604/385.101; 604/385.12
[58] Field of Search ..................... 604/361, 360, 604/359, 358, 362, 367, 378, 385.01, 385.101, 385.12

[56] References Cited

U.S. PATENT DOCUMENTS

| | | | |
|---|---|---|---|
| 2,127,538 | 8/1938 | Seiger | 128/138 |
| 2,926,667 | 3/1960 | Burger et al. | 128/285 |
| 4,335,722 | 6/1982 | Jackson | 128/285 |
| 4,356,818 | 11/1982 | Macias et al. | 123/138 |
| 4,401,712 | 8/1983 | Morrison | 428/289 |
| 4,636,474 | 1/1987 | Ogura et al. | 435/291 |
| 4,681,577 | 7/1987 | Stern et al. | 604/378 |
| 4,705,050 | 11/1987 | Markham | 128/749 |
| 4,747,166 | 5/1988 | Kuntz | 4/144.1 |
| 4,753,645 | 6/1988 | Johnson | 604/378 |
| 4,776,331 | 10/1988 | Simjian | 128/169 |
| 4,778,459 | 10/1988 | Fuisz | 604/378 |
| 4,787,896 | 11/1988 | Houghton et al. | 604/385.1 |
| 4,842,593 | 6/1989 | Jordan et al. | 604/360 |
| 4,852,578 | 8/1989 | Companion et al. | 128/661.03 |
| 4,968,312 | 11/1990 | Khan | 604/388.1 |
| 5,002,541 | 3/1991 | Conkling et al. | 604/319 |
| 5,103,835 | 4/1992 | Yamada et al. | 128/734 |
| 5,678,564 | 10/1997 | Lawrence et al. | 128/761 |
| 5,702,428 | 12/1997 | Tippey et al. | 607/41 |
| 5,722,931 | 3/1998 | Heaven | 660/29 |
| 5,733,272 | 3/1998 | Brunner et al. | 604/359 |
| 5,760,694 | 6/1998 | Nissim et al. | 340/604 |
| 5,769,834 | 6/1998 | Reiter et al. | 604/385.1 |
| 5,876,393 | 3/1999 | Ahr et al. | 604/387 |

FOREIGN PATENT DOCUMENTS

| | | | |
|---|---|---|---|
| 0 286 374 | 10/1988 | European Pat. Off. | A61B 5/00 |
| 0 610 951 | 8/1994 | European Pat. Off. | A61F 13/20 |
| 0 804 912 | 11/1997 | European Pat. Off. | A61F 13/15 |
| 0 804 913 | 11/1997 | European Pat. Off. | A61F 13/15 |
| 0 804 915 | 11/1997 | European Pat. Off. | A61F 13/15 |
| 0 804 916 | 11/1997 | European Pat. Off. | A61F 13/15 |
| 0 804 917 | 11/1997 | European Pat. Off. | A61F 13/15 |
| 0 806 194 | 11/1997 | European Pat. Off. | A61F 13/15 |
| 0 806 195 | 11/1997 | European Pat. Off. | A61F 13/15 |
| 3 921 784 | 7/1989 | Germany | A61B 5/00 |
| 01277558 | 11/1999 | Japan | A61F 5/44 |
| WO 94/24974 | 11/1994 | WIPO | A61F 13/15 |
| WO 96/14813 | 5/1996 | WIPO | A61F 5/48 |
| WO 96/20681 | 7/1996 | WIPO | A61F 13/15 |
| WO 97/32542 | 9/1997 | WIPO | A61F 2/00 |
| WO 98/22063 | 5/1998 | WIPO | A61F 13/15 |
| WO 98/29079 | 7/1998 | WIPO | A61F 13/15 |
| WO 99/07317 | 2/1999 | WIPO | A61F 13/15 |

*Primary Examiner*—John G. Weiss
*Assistant Examiner*—Miley C. Peppers, III
*Attorney, Agent, or Firm*—David M. Weirich; Steven W. Miller; Thomas J. Osborne, Jr.

[57] ABSTRACT

Disposable articles such as diapers, incontinent briefs, diaper holders and/or inserts, training pants, feminine hygiene garments, tampons, and the like, having a responsive system. The article includes a sensor that detects an input, an actuator that is adapted to perform a responsive function upon the input, and a feedback control loop in which the actuator is adapted to perform the responsive function upon the input when the sensor detects the input.

29 Claims, 9 Drawing Sheets

DISPOSABLE ARTICLE HAVING A RESPONSIVE SYSTEM INCLUDING A FEEDBACK CONTROL LOOP

FIELD OF THE INVENTION

The present invention relates to disposable articles and, more particularly, to disposable articles having a responsive system that includes a feedback control loop.

BACKGROUND OF THE INVENTION

Today, disposable articles, such as diapers, adult incontinence briefs, sanitary napkins and tampons, are widely used in infant and toddler care and in the care of incontinent adults as a means of containing, isolating and disposing of bodily wastes. These articles have generally replaced reusable, washable cloth garments as the preferred means for these applications because of their convenience and reliability.

While many advancements have been made in the field of disposable articles for both infants and adults, which have enabled them to become widely preferred over conventional cloth garments, a number of problems still exist. Among the problems experienced with these disposable articles are leakage of bodily waste (e.g., urine, feces, menses), skin rash and irritation, contamination of large areas of the wearer's skin with feces, difficult cleanup of bodily wastes such as feces, waste odor, lack of customization to individuals (e.g., fit), etc.

Attempts have been made to address these problems. Super absorbent polymers, for example, have been used to increase the ability of an absorbent article to absorb and retain urine. Barrier leg cuffs have also been used to improve fit and reduce leakage. U.S. Pat. No. 3,860,003, entitled "Contractible Side Portions For Disposable Diaper," issued to Kenneth B. Buell on Jan. 14, 1975, for example, describes an elasticized leg cuff disposable diaper that has achieved wide acceptance and commercial success. Disposable articles have also used pockets, barriers, etc. to contain and prevent leakage of feces from the article. See, for example, U.S. Pat. No. 4,695,278, entitled "Absorbent Article Having Dual Cuffs," issued to Michael I. Lawson on Sep. 22, 1987; U.S. Pat. No. 4,795,454, entitled "Absorbent Article Having Leakage-Resistant Dual Cuffs," issued to Jerry L. Dragoo on Jan. 3, 1989; and U.S. Pat. No. 5,540,671, entitled "Absorbent Article Having A Pocket Cuff With An Apex," issued to Dreier on Jul. 30, 1996. Disposable articles having a selectively expandable or inflatable component that is activated at the point of use or in response to an activating liquid such as water or urine to provide fecal void space or displacement of a topsheet to improve fit have also been disclosed. For example, U.S. Pat. No. 5,330,459, entitled "Disposable Absorbent Article Having an Inflatable Spacer," issued to Gary D. LaVon et al. on Jul. 19, 1994 and U.S. Pat. No. 5,520,674, entitled "Disposable Absorbent Article Having a Sealed Expandable Component," issued to Gary D. Lavon et al. on May 28, 1996 describe disposable absorbent articles having a component that is expandable at the point of use or expands in response to an activating liquid such as water or urine. These expandable components, however, are problematic in that they either require action by the caregiver to activate the components or operate continuously and require too much of a liquid activator to fully expand because the expansion is proportional to the amount of the liquid activator. In addition, self-contracting leg gathers have been disclosed that react with a liquid activator such as water or urine. For example, U.S. Pat. No. 4,246,900, entitled "Diaper Including Moisture-Responsive Seal Means," issued to Friedrich-Wilhelm Schroder on Jan. 27, 1981. Again, these self-contracting gathers have the problem that they either require action by the caregiver to activate the components or operate continuously and require too much of a liquid activator to fully contract because the contraction is proportional to the amount of the liquid activator.

SUMMARY OF THE INVENTION

The present invention is directed to a disposable article having a responsive system including a feedback control loop that acts in response to and upon an input such as bodily waste (e.g., to isolate it), a component of bodily waste (e.g., to inhibit enzyme activity of the waste), or pressure, motion, other actions or conditions of the wearer (e.g., to lubricate the skin, etc.). A feedback control loop includes distinct sensor and actuator components and uses a detection or a measurement of an element or a parameter of the output condition as at least one trigger of a responsive function that is performed upon the input. The responsive system of the present invention may be either a continuous or discontinuous responsive system that includes a feedback control loop. In a continuous responsive system, the output is quantitatively dependent upon the quantity of the input, i.e., continuously increasing quantities of the input are required to effect continuously increasing quantities of the output, or where the output of the responsive system comprises a passive release of a stored material. In a discontinuous responsive system, however, the output function is essentially independent of the quantity of the input beyond a threshold level. By acting upon the input to the system, a feedback control loop allows for a desired outcome when the input is detected instead of providing a blind response that is unrelated to the input being detected by the system.

BRIEF DESCRIPTION OF THE DRAWINGS

While the specification concludes with claims that particularly point out and distinctly claim the present invention, it is believed that these claims will be better understood from the following description taken in conjunction with the accompanying drawings in which:

DETAILED DESCRIPTION OF THE INVENTION

As used herein, the term "absorbent article" refers to devices which absorb and contain body exudates, and more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner). (As used herein, the term "disposed" is used to mean that an element(s) of the diaper is formed (joined and positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, article 20, shown in FIG. 1. As used herein, the term "diaper" refers to an absorbent article generally worn by infants and incontinent persons about the lower torso. The present invention is also applicable to other absorbent articles such as incontinence briefs, incontinence undergarments, absorbent inserts, diaper holders and liners, colostomy type bags for a natural or an artificial anus, feminine hygiene garments, tampons, wipes, mops, bandages and the like.

Figure 1:
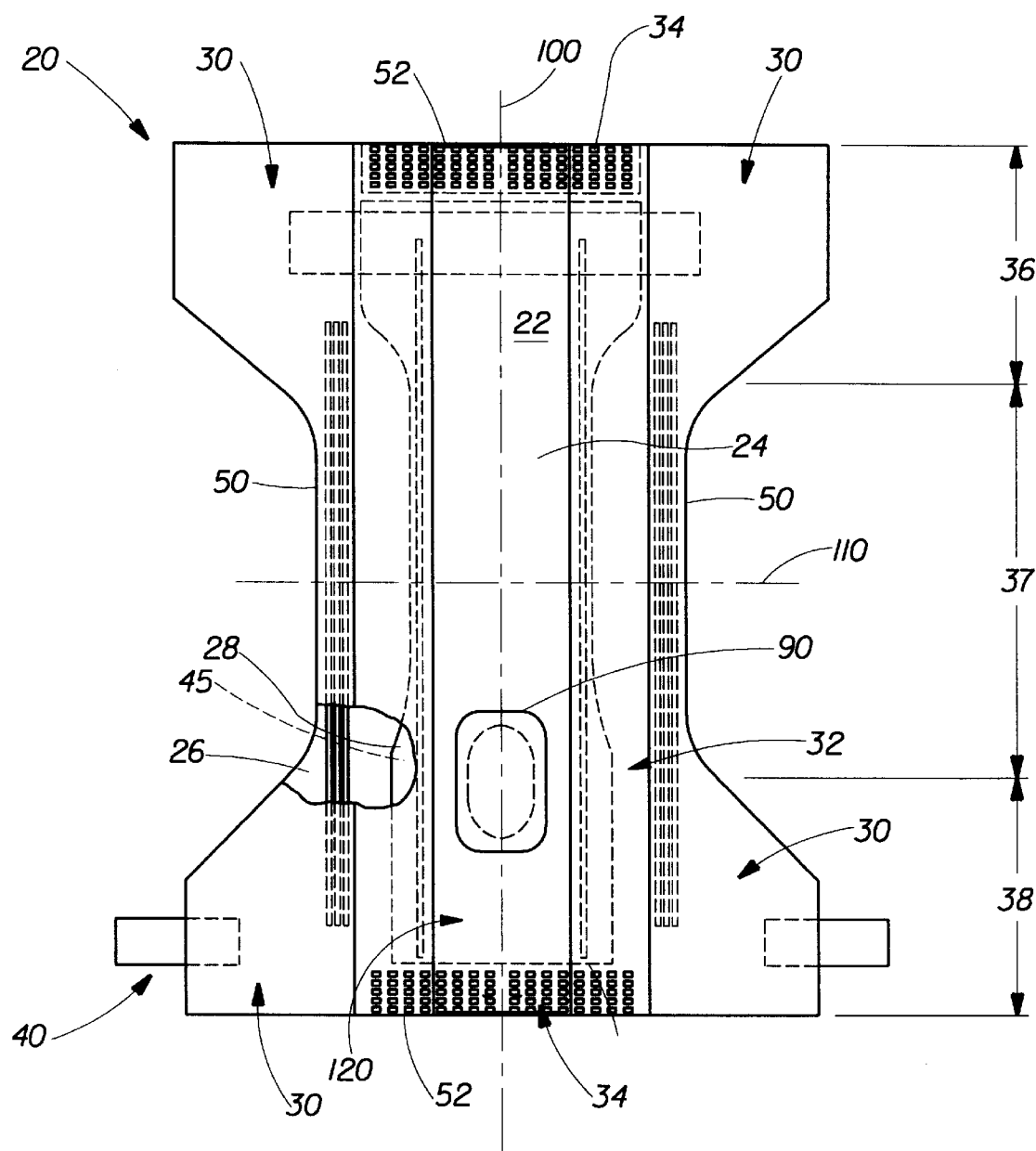
FIG. 1 is a plan view of the article made in accordance with the present invention in a flat-out state with portions of the structure being cut-away to more clearly show the construction of the article, wherein the article is a diaper.

FIG. 1 is a plan view of an article 20 of the present invention, which is shown in this Figure as a diaper, in a flat-out, state with portions of the structure being cut-away to more clearly show the construction of the article 20. The portion of the article 20 which faces the wearer is oriented towards the viewer. As shown in FIG. 1, the article 20 preferably comprises a liquid pervious topsheet 24; a liquid impervious backsheet 26; an absorbent core 28, which is preferably positioned between at least a portion of the topsheet 24 and the backsheet 26; side panels 30; elasticized leg cuffs 32; an elastic waist feature 34; a fastening system generally designated 40 and a bodily waste isolation device 90. Article 20 is shown in FIG. 1 to have a first waist region 36, a second waist region 38 opposed to the first waist region 36 and a crotch region 37 located between the first waist region and the second waist region. The periphery of the article 20 is defined by the outer edges of the article 20 in which the longitudinal edges 50 run generally parallel to the longitudinal centerline 100 of the article 20 and the end edges 52 run between the longitudinal edges 50 generally parallel to the lateral centerline 110 of the article 20.

The chassis 22 of the article 20 comprises the main body of the article 20. The chassis 22 comprises at least a portion of the absorbent core 28 and preferably an outer covering layer including the topsheet 24 and the backsheet 26. If the absorbent article comprises a separate holder and a liner, the chassis 22 generally comprises the holder and the liner. (For example, the holder may comprise one or more layers of material to form the outer cover of the article and the liner may comprise an absorbent assembly including a topsheet, a backsheet, and an absorbent core. In such cases, the holder and/or the liner may include a fastening element which is used to hold the liner in place throughout the time of use.) For unitary absorbent articles, the chassis 22 comprises the main structure of the diaper with other features added to form the composite diaper structure. While the topsheet 24, the backsheet 26, and the absorbent core 26 may be assembled in a variety of well known configurations, preferred diaper configurations are described generally in U.S. Pat. No. 3,860,003 entitled "Contractible Side Portions for Disposable Diaper" which issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" which issued to Roe et al. on Sep. 10, 1996; U.S. Pat. No. 5,569,234 entitled "Disposable Pull-On Pant" which issued to Buell et al. on Oct. 29, 1996; U.S. Pat. No. 5,580,411 entitled "Zero Scrap Method For Manufacturing Side Panels For Absorbent Articles" which issued to Nease et al. on Dec. 3, 1996; and U.S. patent application Ser. No. 08/915,471 entitled "Absorbent Article With Multi-Directional Extensible Side Panels" filed Aug. 20, 1997 in the name of Robles et al.; each of which is incorporated herein by reference.

The backsheet 26 is generally that portion of the article 20 positioned adjacent the garment facing surface 45 of the absorbent core 28 which prevents the exudates absorbed and contained therein from soiling articles which may contact the article 20, such as bedsheets and undergarments. In preferred embodiments, the backsheet 26 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962 and X10964. Other suitable backsheet materials may include breathable materials which permit vapors to escape from the article 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont and copending U.S. patent application Ser. No. 08/744,487, filed on Nov. 6, 1996 in the name of Curro. Other breathable backsheets including nonwoven webs and apertured formed films are described in U.S. Pat. No. 5,571,096 issued to Dobrin et al. on Nov. 5, 1996. Each of these references is hereby incorporated by reference herein. In some embodiments such as an insert for article 20, however, the backsheet may be liquid pervious and may, for example, include the same materials as described with respect to topsheet 24 below.

The backsheet 26, or any portion thereof, may be elastically extensible in one or more directions. In one embodiment, the backsheet 26 may comprise a structural elastic-like film ("SELF") web. A structural elastic-like film web is an extensible material that exhibits an elastic-like behavior in the direction of elongation without the use of added elastic materials. The SELF web includes a strainable network having at least two contiguous, distinct, and dissimilar regions. Preferably, of the regions is configured so that it will exhibit resistive forces in response to an applied axial elongation in a direction parallel to the predetermined axis before a substantial portion of the other region develops significant resistive forces to the applied elongation. At least one of the regions has a surface-pathlength which is greater than that of the other region as measured substantially parallel to the predetermined axis while the material is in an untensioned condition. The region exhibiting the longer surface-pathlength includes one or more deformations which extend beyond the plane of the other region. The SELF web exhibits at least two significantly different stages of controlled resistive force to elongation along at least one predetermined axis when subjected to an applied elongation in a direction parallel to the predetermined axis. The SELF web exhibits first resistive forces to the applied elongation until the elongation of the web is sufficient to cause a substantial portion of the region having the longer surface-pathlength to enter the plane of applied elongation, whereupon the SELF web exhibits second resistive forces to further elongation. The total resistive forces to elongation are higher than the first resistive forces to elongation provided by the first region. SELF webs suitable for the present invention are more completely described in U.S. Pat. No. 5,518,801 entitled Web Materials Exhibiting Elastic-Like Behavior, which issued to Chappell, et, al. on May 21, 1996, which is incorporated herein by reference. In alternate embodiments, the backsheet 26 may comprise elastomeric films, foams, strands, or combinations of these or other suitable materials with nonwovens or synthetic films.

The backsheet 26 may be joined to the topsheet 24, the absorbent core 28 or any other element of the article 20 by any attachment means known in the art. For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986 entitled "Disposable Waste-Containment Garment", which issued to Minetola et al. on Mar. 4, 1986. Other suitable attachment means include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Adhesives which have been found to be satisfactory are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

The topsheet 24 is preferably positioned adjacent the body surface 47 of the absorbent core 28 and may be joined thereto and/or to the backsheet 26 by any attachment means known in the art. Suitable attachment means are described above with respect to means for joining the backsheet 26 to other elements of the article 20. In one preferred embodiment of the present invention, the topsheet 24 and the backsheet 26 are joined directly to each other in some locations and are indirectly joined together in other locations by directly joining them to other elements of the article 20.

The topsheet 24 is preferably compliant, soft feeling, and non-irritating to the wearer's skin. Further, at least a portion of the topsheet 24 is liquid pervious, permitting liquids to readily penetrate through its thickness. A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. If the topsheets include fibers, the fibers may be spunbond, carded, wet-laid, meltblown, hydroentangled, or otherwise processed as is known in the art. One suitable topsheet 24 comprising a web of staple length polypropylene fibers is manufactured by Veratec, Inc., a Division of International Paper Company, of Walpole, Mass. under the designation P-8.

Suitable formed film topsheets are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; and U.S. Pat. No. 5,006,394 "Multilayer Polymeric Film" issued to Baird on Apr. 9, 1991. Other suitable topsheets 30 are made in accordance with U.S. Pat. Nos. 4,609,518 and 4,629,643 which issued to Curro et al. on Sep. 2, 1986 and Dec. 16, 1986, respectively, and both of which are incorporated herein by reference. Such formed films are available from The Procter & Gamble Company of Cincinnati, Ohio as "DRI-WEAVE" and from Tredegar Corporation of Terre Haute, Ind. as "CLIFF-T."

Preferably, the topsheet 24 is made of a hydrophobic material or is treated to be hydrophobic in order to isolate the wearer's skin from liquids contained in the absorbent core 28. If the topsheet 24 is made of a hydrophobic material, preferably at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 28. The topsheet 24 can be rendered hydrophilic by treating it with a surfactant or by incorporating a surfactant into the topsheet. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991. A more detailed discussion of some suitable methods for incorporating surfactant in the topsheet can be found in U.S. Statutory Invention Registration No. H1670, published on Jul. 1, 1997 in the names of Aziz et al. Each of these references is hereby incorporated by reference herein. Alternatively, the topsheet 24 may include an apertured web or film which is hydrophobic. This may be accomplished eliminating the hydrophilizing treatment step from the production process and/or applying a hydrophobic treatment to the topsheet 24, such as a polytetraflouroethylene compound like SCOTCHGUARD or a hydrophobic lotion composition, as described below. In such embodiments, it is preferred that the apertures be large enough to allow the penetration of aqueous fluids like urine without significant resistance.

Any portion of the topsheet 24 may be coated with a lotion as is known in the art. Examples of suitable lotions include those described in U.S. Pat. Nos. 5,607,760 entitled "Disposable Absorbent Article Having A Lotioned Topsheet Containing an Emollient and a Polyol Polyester Immobilizing Agent" which issued to Roe on Mar. 4, 1997; U.S. Pat. No. 5,609,587 entitled "Diaper Having A Lotion Topsheet Comprising A Liquid Polyol Polyester Emollient And An Immobilizing Agent" which issued to Roe on Mar. 11, 1997; U.S. Pat. No. 5,635,191 entitled "Diaper Having A Lotioned Topsheet Containing A Polysiloxane Emollient" which issued to Roe et al. on Jun. 3, 1997; and U.S. Pat. No. 5,643,588 entitled "Diaper Having A Lotioned Topsheet" which issued to Roe et al. on Jul. 1, 1997. The lotion may function alone or in combination with another agent as the hydrophobizing treatment described above. The topsheet may also include or be treated with antibacterial agents, some examples of which are disclosed in PCT Publication No. WO 95/24173 entitled "Absorbent Articles Containing Antibacterial Agents in the Topsheet For Odor Control" which was published on Sep. 14, 1995 in the name of Theresa Johnson. Further, the topsheet 24, the backsheet 26 or any portion of the topsheet or backsheet may be embossed and/or matte finished to provide a more cloth like appearance.

The absorbent core 28 may comprise any absorbent material which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or crosslinked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 28 may also be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures). However, the total absorbent capacity of the absorbent core 28 should be compatible with the design loading and the intended use of the article 20.

Exemplary absorbent structures for use as the absorbent core are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735, entitled "High Density Absorbent Members Having Lower Density and Lower Basis Weight Acquisition Zones", issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" which issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997. Each of these patents is incorporated herein by reference.

The article 20 may also comprise at least one elastic waist feature 34 that helps to provide improved fit and containment. The elastic waist feature 34 is generally intended to elastically expand and contract to dynamically fit the wearer's waist. The elastic waist feature 34 preferably extends at least longitudinally outwardly from at least one waist edge 62 of the absorbent core 28 and generally forms at least a portion of the end edge 52 of the article 20. Disposable diapers are often constructed so as to have two elastic waist features, one positioned in the first waist region 36 and one positioned in the second waist region 38. Further, while the elastic waist feature 34 or any of its constituent elements may comprise one or more separate elements affixed to the article 20, the elastic waist feature 34 may be constructed as an extension of other elements of the article 20, such as the backsheet 26, the topsheet 24, or both the backsheet 26 and the topsheet 24.

The elastic waist feature 34 may be constructed in a number of different configurations including those described in U.S. Pat. No. 4,515,595 issued to Kievit et al. on May 7, 1985; U.S. Pat. No. 4,710,189 issued to Lash on Dec. 1, 1987; U.S. Pat. No. 5,151,092 issued to Buell on Sep. 9, 1992; and U.S. Pat. No. 5,221,274 issued to Buell on Jun. 22, 1993. Other suitable waist configurations may include waistcap features such as those described in U.S. Pat. No. 5,026,364 issued to Robertson on Jun. 25, 1991 and U.S. Pat. No. 4,816,025 issued to Foreman on Mar. 28, 1989. All of the above mentioned references are incorporated herein by reference.

The article 20 may also include a fastening system 40. The fastening system 40 preferably maintains the first waist region 36 and the second waist region 38 in an overlapping configuration so as to provide lateral tensions about the circumference of the article 20 to hold the article 20 on the wearer. The fastening system 40 preferably comprises tape tabs and/or hook and loop fastening components, although any other known fastening means are generally acceptable. Some exemplary fastening systems are disclosed in U.S. Pat. No. 3,848,594 entitled "Tape Fastening System for Disposable Diaper" issued to Buell on Nov. 19, 1974; U.S. Pat. No. B1 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; and the herein before referenced U.S. Pat. No. 5,151,092 issued to Buell on Sep. 9, 1992; and U.S. Pat. No. 5,221,274 issued to Buell on Jun. 22, 1993. The fastening system may also provide a means for holding the article in a disposal configuration as disclosed in U.S. Pat. No. 4,963,140 issued to Robertson et al. on Oct. 16, 1990. Each of these patents is incorporated herein by reference. In alternative embodiments, opposing sides of the garment may be seamed or welded to form a pant. This allows the article to be used as a pull-on type diaper, such as a training pant.

The article 20 may also comprise side panels 30. The side panels 30 may be elastic or extensible to provide a more comfortable and contouring fit by initially conformably fitting the article 20 to the wearer and sustaining this fit throughout the time of wear well past when the article 20 has been loaded with exudates since the elasticized side panels 30 allow the sides of the article 20 to expand and contract. The side panels 30 may also provide more effective application of the article 20 because even if the diaperer pulls one elasticized side panel 30 farther than the other during application, the article 20 will "self-adjust" during wear.

While the article 20 of the present invention preferably has the side panels 30 disposed in the second waist region 38, the article 20 may be provided with side panels 30 disposed in the first waist region 36 or in both the first waist region 36 and the second waist region 38. The side panels 30 may be constructed in any suitable configurations. Examples of diapers with elasticized side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151,092 issued to Buell on Sep. 9, 1992; and U.S. Pat. No. 5,221,274 issued to Buell on Jun. 22, 1993; U.S. Pat. No. 5,669,897 issued to LaVon, et al. on Sep. 23, 1997 entitled "Absorbent Articles Providing Sustained Dynamic Fit"; U.S. patent application Ser. No. 08/915,471 entitled "Absorbent Article With Multi-Directional Extensible Side Panels" filed Aug. 20, 1997 in the names of Robles, et al.; each of which is incorporated herein by reference.

The article 20 preferably further includes leg cuffs 32 which provide improved containment of liquids and other body exudates. Leg cuffs may also be referred to as leg bands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. on Feb. 28, 1989 and Mar. 20, 1990, respectively, describe disposable diapers having "stand-up" elasticized flaps (barrier cuffs) which improve the containment of the leg regions. U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs and barrier cuffs. In some embodiments, it may be desirable to treat all or a portion of the leg cuffs with a lotion, as described above.

Embodiments of the present invention may also include pockets for receiving and containing waste, spacers which provide voids for waste, barriers for limiting the movement of waste in the article, compartments or voids which accept and contain waste materials deposited in the diaper, and the like, or any combinations thereof. Examples of pockets and spacers for use in absorbent products are described in U.S. Pat. No. 5,514,121 issued to Roe et al. on May 7, 1996, entitled "Diaper Having Expulsive Spacer"; U.S. Pat. No. 5,171,236 issued to Dreier et al on Dec. 15, 1992, entitled "Disposable Absorbent Article Having Core Spacers"; U.S. Pat. No. 5,397,318 issued to Dreier on Mar. 14, 1995, entitled "Absorbent Article Having A Pocket Cuff"; U.S. Pat. No. 5,540,671 issued to Dreier on Jul. 30, 1996, entitled "Absorbent Article Having A Pocket Cuff With An Apex"; and PCT Application WO 93/25172 published Dec. 3, 1993, entitled "Spacers For Use In Hygienic Absorbent Articles And Disposable Absorbent Articles Having Such Spacer"; and U.S. Pat. No. 5,306,266, entitled "Flexible Spacers For Use In Disposable Absorbent Articles", issued to Freeland on Apr. 26, 1994. Examples of compartments or voids are disclosed in U.S. Pat. No. 4,968,312, entitled "Disposable Fecal Compartmenting Diaper", issued to Khan on Nov. 6, 1990; U.S. Pat. No. 4,990,147, entitled "Absorbent Article With Elastic Liner For Waste Material Isolation", issued to Freeland on Feb. 5, 1991; U.S. Pat. No. 5,62,840, entitled "Disposable Diapers", issued to Holt et al on Nov. 5, 1991; and U.S. Pat. No. 5,269,755 entitled "Trisection Topsheets For Disposable Absorbent Articles And Disposable Absorbent Articles Having Such Trisection Topsheets", issued to Freeland et al on Dec. 14, 1993. Examples of suitable transverse barriers are described in U.S. Pat. No. 5,554,142 entitled "Absorbent Article Having Multiple Effective Height Transverse Partition" issued Sep. 10, 1996 in the name of Dreier et al.; PCT Patent WO 94/14395 entitled "Absorbent Article Having An Upstanding Transverse Partition" published Jul. 7, 1994 in the name of Freeland, et al.; and U.S. Pat. No. 5,653,703 Absorbent Article Having Angular Upstanding Transverse Partition, issued Aug. 5, 1997 to Roe, et al. All of the above-cited references are hereby incorporated by reference herein.

The article 20 preferably also includes at least one sensor 60. As used in this application, the term "sensor" refers to a device that is used to detect an event or a parameter that is associated with an event. A parameter associated with an event is any measureable signal that correlates with the occurrence of an event within the frame of reference of the system (i.e., a signal caused by the waste, the wearer, or a component thereof). Sensors include anything that responds to one or more specific inputs. Examples of inputs that may be detected by the sensor of the present invention include, but are not limited to, attitude, pressure, motion, moisture, enzymes, bacteria, pH, conductivity, resistance, capacitance, inductance, or other chemical, biochemical, biological, mechanical or electrical properties and/or components of bodily wastes. The sensors preferably detect "non-environmental" inputs such as a non-thermal or a non-relative humidity input in order to minimize the number of false responses by minimizing the possibility of an environmental condition triggering the sensor instead of the sensor detecting an input caused by the waste, the wearer, or a component thereof. An electrical or biological sensor may, for example, detect an elimination of bodily waste event such as a defecation, urination or discharge of menses by sensing a component of the waste. A sensor may detect one or more events or one or more parameters associated with an event and provide an input to an actuator or a controller. Further, a sensor of the present invention may also be reversible or irreversible. A dissolving film or capsule is an example of an irreversible sensor, while an electrical sensor that detects electrical activity in muscles of the wearer may receive multiple sequential input signals (i.e., is reversible).

As discussed above, sensors 60 of the present invention may include anything that responds to a specific input. For example, the sensor 60 of the present invention may be chemical, mechanical, electrical, etc. A chemical sensor may respond to chemical and/or biochemical inputs such as enzymes typically present in bodily wastes, pH, water, biological inputs such as bacteria, blood or any one or more other components of bodily wastes such as feces, urine, or menses, etc. A chemical sensor may use a chemical reaction as a detection means or may involve a dissolution of a material soluble in an input material of interest. Examples of chemical or biological sensors include dissolving or rupturable films, capsules, cells, seals, etc. that dissolve or rupture in response to a specific chemical, biochemical or biological input or to a specific class of chemical, biochemical or biological inputs. A mechanical sensor may also respond to motion, attitude, pressure, etc. An example of a mechanical sensor is a bellows-type in which when a baby sits on the sensor the weight pushes down on the bellows to inflate a portion of the sensor. A mechanical sensor may also include a sensor or a portion of the sensor that is broken or separated under a pre-defined applied pressure. An electrical sensor may also be used to respond to moisture, urine, feces, menses, pressure, resistance, capacitance, inductance, etc. An electrical sensor may, for example, include a sensor in which a conductive input such as urine or feces completes an electrical circuit; a sensor in which the input such as pressure or tension closes an electrical contact to complete a circuit; a piezoelectric sensor that generates a signal via pressure induced by the wearer or a part of the wearer (e.g., from motion or muscle tone); a sensor in which the resistance, capacitance or inductance varies in the presence of the input to which the sensor responds; or a sensor that receives electrical signals from the body (e.g., from the subcutaneous muscles) of the wearer through a contact such as a skin contact sensor. Optionally, the sensor may be a biosensor as known in the art (e.g., an enzyme sensor, organella sensor, tissue sensor, microorganism sensor, or electrochemical sensor). The sensor may be adapted to detect proteins, sugars, bile components, etc. such as described in U.S. Pat. No. 4,636,474 entitled "Toilet Apparatus," issued to Kenji Ogura et al. on Jan. 13, 1987. Biosensors may comprise bio-recognition systems, typically enzymes or binding proteins such as antibodies immobilized onto the surface of physico-chemical transducers. The biosensors may detect components of bodily wastes, such as ammonia and phenol (e.g., via biosensors comprising enzyme electrodes). A specific strain of bacteria may be detected via biosensors employing antibodies raised against that bacterial strain. Exemplary enzyme electrodes that may be used to detect phenols (e.g. in urine or feces) include tyrosinase based electrodes or polyphenol oxidase enzyme electrodes described in U.S. Pat. No. 5,676,820 entitled "Remote Electrochemical Sensor," issued to Joseph Wang et al. on Oct. 14, 1997 and U.S. Pat. No. 5,091,299 entitled "An Enzyme Electrode For Use In Organic Solvents," issued to Anthony P. F. Turner et al. on Feb. 25, 1992, respectively.

Optionally, the sensor 60 may be a "proactive sensor" that is capable of detecting changes or signals in or on the body of the wearer, in the article or in the waste, i.e., inputs that directly relate or, at a minimum, correlate to the occurrence of an impending event such as a defecation, urination or other discharge of bodily waste. A proactive sensor, for example, may detect an impending event such as a defecation, urination or discharge or a parameter that correlates to such an event. The impending event may be related to the bodily waste, the wearer, the article, or a component or components thereof. A parameter that correlates to an event is any measurable input signal that correlates with the occurrence of the event within the frame of reference of the system (i.e., a signal caused by the waste or the wearer). The proactive sensor may, for example, predict the occurrence of a defecation, urination or discharge of bodily waste or may detect signals that may precede skin rash or irritation. Proactive sensors in an article may measure many different inputs in order to predict an event. For example, the proactive sensor may monitor the external anal sphincter muscle for a relaxation in the anal sphincter that precedes the release of feces and/or urine, a separation of the buttocks, a pressure change in the abdomen, a gas concentration in the article, or any other indication that may be used to predict or anticipate the occurrence of an event such as a defecation, a urination or a discharge of bodily wastes. Alternatively, a proactive sensor of the present invention may detect signals that precede skin irritation. For example, the sensor may detect residual fecal contamination of the wearer's skin (e.g., fecal enzyme residue left after cleaning up a soiled diaper) that may, over time, lead to irritated skin. Detection of a high pH, an increased skin hydration resulting in a measurable increase in conductance or decrease in impedance of skin, etc. may also be used to predict potential skin irritation. Further embodiments of a proactive sensor are described in copending U.S. application Ser. No. 09/107,561 entitled "Disposable Article Having A Proactive Sensor" (P&G Case No. 7196) filed on Jun. 29, 1998, which is herein incorporated by reference.

The sensor 60 may be disposed in and/or operatively connected to any portion of a disposable article that will be exposed to the input that the sensor is designed to detect. For the purposes of the present invention, the term "operatively connected" refers to a means of communication such that the sensor 60 may signal some portion of the article 20 when the sensor 60 detects an input. The sensor 60 may be separate from and operatively connected to another portion of the sensor 60, another sensor 60, an actuator 70, a controller 80 or some other portion or component of the article 20. "Operatively connected" may, for example, include a means of communication such as an electrical connection via a conductive wire or member, via a transmitted signal such as radio frequency, infrared or another transmitted frequency communication. Alternatively, the sensor 60 may be operatively connected via a mechanical connection such as a pneumatic or a hydraulic connection.

In article 20, for example, the sensor 60 may be located in the front waist region 36, the rear waist region 38 or the crotch region 37 of article 20, and may be integral with, disposed adjacent to, joined to, or comprise a portion of the chassis 22, the topsheet 24, the backsheet 26, the absorbent core 28, side panels 30, leg cuffs 32, a waist feature 34, a fastening system 40, the longitudinal 50 or end 52 edges, etc. The sensor 60 may be integral with the article 20, or may be installed by the caretaker or the wearer. The sensor 60 may be completely contained within the article such as article 20 or may have a receiving portion located in the article such that it will come into contact with the desired input and another portion such as a transmitting portion located either in the article or outside the article. The sensor 60 may be external to the article 20 yet operatively connected to some portion of the article 20 such that the sensor 60 may detect an input external to the article 20 and provide a signal to a controller 80 and/or an actuator 70. In some embodiments, the sensor may be separate from the article, e.g., separately applied to some portion of the wearer, and/or may have one or more component separate from the article.

The sensor 60 may further comprise a sensing "system" including two or more sensors, each of which may detect the same or different signals from the same or different sources. The sensing system may include components that are located inside, external to and/or separate from the article. For example, the sensing system may include a sensor inside the article that detects electrical signals in the external anal sphincter of the wearer and a sensor external to the article that detects motion, tension or muscle activity in the abdomen of the wearer. The sensing system may also or alternatively include components other than the sensing elements inside, external to and/or separate from the article. The sensing system, for example, may include a transmitter that is external to the article and transmits a signal to another part of the sensing system that is joined to or disposed in the article 20.

The article 20 preferably also comprises an actuator 70. As used in this application, the term "actuator" refers to a device that comprises "potential" and a means of transforming that potential to perform or activate a "responsive function." The potential of the actuator 70 may comprise either stored or potential energy or stored material. The actuator 70 thus may perform or activate a responsive function by transforming potential energy to kinetic energy or by releasing or delivering a stored material. A "responsive function" is defined for the purposes of this application as a function performed upon an input consisting of the bodily waste, the wearer, the article, or a component or components thereof. For the purposes of the present invention, a function is considered to be performed upon the input if the function is performed upon the element sensed, e.g., sensing pH and acting upon the pH, or may include acting upon a composition of which the element sensed is an integral component, e.g., sensing a fecal enzyme or fecal moisture and acting upon feces. A device that merely provides a signal indicating that an event has occurred, however, is not considered an "actuator" as defined for the purposes of this application. A component of bodily waste may include, for example, moisture, electrolytes, enzymes, volatile gases, bacteria, blood, etc. A component of the wearer may also include skin, genitalia, the anus, the anal sphincter muscle, etc. A component of the article may also include leg cuffs, waist cuffs or other waste barriers and/or containment components, side panels, ears, a chassis, an absorbent core, an acquisition component, a fastening system, the longitudinal or end edges, etc. Potential energy may be stored as mechanical, electrical, chemical or thermal energy. "Kinetic energy" as used in this application refers to the capacity to do work or to perform a responsive function as described above (e.g., expansion of a compressed device, rotation of a twisted device, a gel that moves as it changes phases, coating or treatment of skin or feces, inhibition of an enzyme, adjustment of pH, etc.).

Triggering the creation of a three dimensional structure to capture waste, for example, involves responsive functions performed on a component of the article and, ultimately, on the waste. Capturing waste, wiping the skin of the wearer or treating the skin with a skin care composition, for example, are responsive functions performed on the waste and/or the wearer. Adjusting the article's geometry (in one, two or three dimensions) or physical properties (e.g., bending modulus, geometry, etc.) are examples of responsive functions, which may be performed on the article. Signaling a caretaker and/or the wearer that an event has occurred, however, does not perform a responsive function because it does not perform a function upon the input. Signaling devices require an agent external to the system (e.g., a human, etc.) to act as an actuator to result in a function being performed. An actuator of a disposable article may, for example, release or deliver a deodorant, enzyme inhibitor, skin care composition or pH control agent; capture, wipe, cover, trap, immobilize, seal, pump, or store bodily waste; or trigger the release or creation of a structure or element designed to perform one or more of these functions or any other responsive function upon the waste, wearer, article, or a component thereof.

An actuator 70 of the present invention may release potential energy to perform or activate a responsive function upon the input. The release of potential energy may transform mechanical, electrical, chemical or thermal potential energy into mechanical, electrical or chemical kinetic energy to perform the responsive function. Actuators may be triggered by a threshold level of an input to release potential energy to perform a responsive function upon the input or may respond continuously upon the input as described below. For example, a compressed foam has stored compressive mechanical potential energy and may provide mechanical kinetic energy when it is released. A twisted foam has stored torsional mechanical potential energy that may provide mechanical kinetic energy, i.e., rotation, when it is released. In addition, stored chemical, electrical or thermal energy may be used to release electrical, mechanical, chemical or thermal kinetic energy. An actuator of a disposable article, for example, may include one or more of the following: stored lotion, feces modification agents, enzyme inhibitors, pH buffers, dyes, pressurized gas, a compressed foam, a pump, an electrically sensitive gel, a pH sensitive gel, a salt concentration sensitive gel, etc. Potential energy may be stored in any manner sufficient to maintain/restrain it until it is required. Examples include batteries and/or capacitors, elastically, torsionally, compressively tensioned materials or structures, in the form of unreacted reagents, and materials capable of performing physical or chemical functions (e.g., absorbents, emollients, pH buffers, enzyme inhibitors, feces modification agents; compressed gases, etc.).

Alternatively, an actuator 70 of the present invention may comprise a quantity of a stored material that has the capacity to perform or activate a responsive function upon the input. In one embodiment, for example, the actuator 70 may passively release or actively deliver a stored material that performs a responsive function upon the input. In this embodiment, the actuator 70 may be triggered by a threshold level of an input to discontinuously release or deliver the stored material at a given time or may release or deliver the material continuously. The actuator 70 may, for example, include stored lotion, skin care compositions, feces modification agents, enzyme inhibitors, pH buffers, dyes, etc. In certain preferred embodiments, the material may be delivered by an actuator 70 such as an expanding resilient material, a released high pressure gas, etc.

In alternative embodiments the sensor and/or actuator may comprise a closed system liquid transport member. A "closed system liquid transport member" or "transport member" comprises a liquid filled member having an inlet port and outlet port, which upon receipt of even a little amount of liquid at the inlet port practically immediately releases liquid at the outlet port. The liquid released from the outlet port may serve as an input signal to a sensor. For example, the liquid may be water, which is released when the transport member imbibes fecal moisture at an inlet port, which acts to dissolve a seal to release stored mechanical energy to create a feces void space. In another embodiment, the transport member may imbibe urine at an inlet port and transport the urine to another portion of the article for storage. Alternatively, the transport member may itself trigger an actuator (e.g., mix with agents to perform a chemical reaction), or may perform at least a portion of the actuator function (e.g., the released water is imbibed by a super absorbent polymer arranged in a particular geometry, which swells and forms a feces void volume). Liquid transport through such transport members is based upon direct suction rather than on capillarity. The liquid is transported through a region into which no significant quantity of air (or other gas) may enter. The driving force for liquid flowing through such a member can be created by a liquid sink (e.g., a capillary or osmotic absorbent structure) or source in liquid connection with the member. Thus, a liquid transport member must have a relatively high liquid permeability.

There are preferably at least two regions within the transport member with different pore sizes, namely the one or more port region(s) having smaller pores and the inner region having a much larger pore size. The inner region of the transport member has a permeability that is relatively high compared to the permeability of a port region (a higher liquid permeability provides less flow resistance), which can be a part of an outer/wall region circumscribing the inner/bulk region. Nonlimiting examples of high porosity materials suitable for use as the inner region material include fibrous structures comprising polyolefin, PET, cellulose, and cellulose-based fibers, and porous, open celled foam such as reticulated foams, cellulose sponges, polyurethane foams, and HIPE foams. In one embodiment, the voids of the inner region are essentially completely filled with an essentially incompressible fluid. The term "essentially completely" refers to the situation, where sufficient void volume of the inner region is filled with the liquid such that a continuous flow path between inlet and outlet ports can be established.

The port regions of the transport member comprise materials which are permeable for the transport liquid, but not for the ambient gas (like air) once they are wetted with the transport liquid. Often, such materials are described as membranes, which are defined as regions that are permeable for liquid, gas or a suspension of particles in a liquid or gas. The membrane may for example comprise a microporous region to provide liquid permeability through the capillaries. In an alternative embodiment, the membrane may comprise a monolithic region comprising a block-copolymer through which the liquid is transported via diffusion. Exemplary membranes for the port regions include celluloseacetate membranes, such as also disclosed in U.S. Pat. No. 5,108,383 entitled "Membranes For Absorbent Articles" issued to White on Apr. 28, 1992, PET films as disclosed in EP-A-0451797, nitrocellulose membranes, cellulosenitrate membranes, PTFE membranes, polyamide membranes, and polyester. Other suitable materials are woven polymeric meshes, such as polyamide or polyethylene meshes as available from Verseidag in Geldern-Waldbeck, Germany, or SEFAR in Rüschlikon, Switzerland.

Figure 10A:
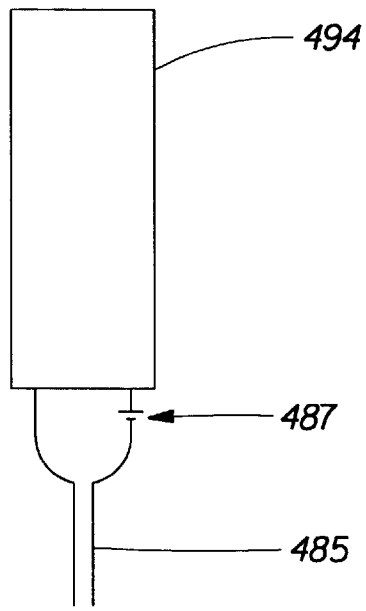
FIGS. 10A and 10B show an embodiment of a responsive system of the present invention including an electrically sensitive gel.
Figure 10B:
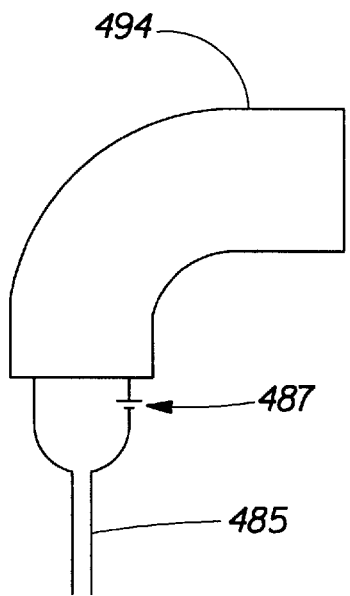
Figure 11A:
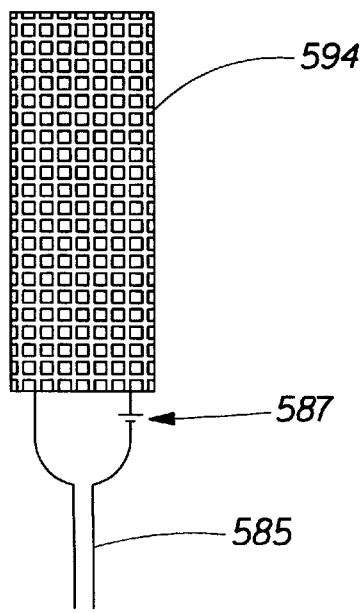
FIGS. 11A, 11B and 11C show another embodiment of a responsive system of the present invention including an electrically sensitive gel.
Figure 11B:
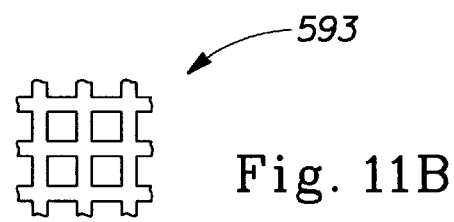
Figure 11C:
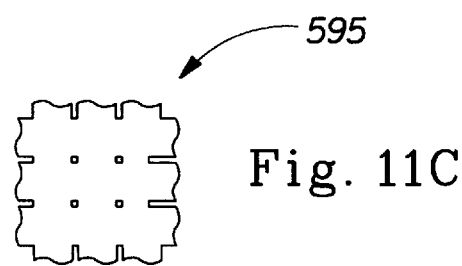

The actuator 70 may alternatively comprise an electrically sensitive gel. Electrically sensitive gels are polymeric gel networks that, when at least partially swollen with water, change volume and/or geometry under the application of an electric current or field. For example, certain partially ionized polyacrylamide gels will undergo anisotropic contraction of about 50% under weak electric fields (e.g., 0.5 volts/cm) when immersed in acetone and water. Alternative electrically sensitive gels may undergo electrically induced bending in the presence of water and a surfactant or may undergo an oscillating wave motion when subjected to an oscillating electric field. It is believed that local shrinkage may be induced in a portion of the gel, e.g., one side of a gel element, by concentrating positively charged surfactant molecules on the negatively charged gel polymer in an electric field. Changing the intensity and/or the polarity of the field induces a movement in the gel as one side decreases in length (e.g., a gel formed in a strip may curl). Electrically sensitive gels may comprise variable geometries such as rectangular, circular, reticulated grid, etc. patterns in order to provide a valve to release a material, allow a bodily waste to flow through, prevent a bodily waste from flowing through, encapsulate a bodily waste, etc. as they change volume and/or geometry. An electrically sensitive gel formed in a strip, for example, may be bent to transport feces when fecal moisture is detected. In FIGS. 10A and 10B, for example, a strip of electrically sensitive gel 494 is shown in a circuit in which fecal moisture may bridge the contacts 485 and allow current to flow from battery 487 to the electrically sensitive gel 494 either bending or straightening the strip. Alternatively, an electrically sensitive gel formed in a reticulated grid pattern, such as shown in FIGS. 11A, 11B and 11C, may be electrically induced to swell or shrink when urine is detected to form a valve that allows and/or prevents urine flow to another portion of the article 20. FIG. 11A, for example, shows a circuit including a reticulated grid pattern of an electrically sensitive gel 594. FIGS. 11B and 11C further show a microscopic view of the grid in a shrunk 593 and in a swollen 594 configuration, respectively. An exemplary material is a weakly cross-linked PAMPs gel (poly (acrylamido-2-methyl propane) sulphonic acid). This type of gel may perform various functions such as the creation of a void space for feces, wiping the skin, applying or delivering a chemical feces treatment agent, or functioning as a valve to release a material. Other exemplary electrically sensitive gels are described in U.S. Pat. No. 5,100,933 issued to Tanaka on Mar. 31, 1990 and WO 9202005. Alternatively, pH sensitive gels or salt concentration sensitive gels that change volume and/or geometry at specific pH or salt concentrations, respectively, may be used as an actuator of the present invention.

An embodiment of an article of the present invention may include one or more proactive sensors and one or more actuators 70. By detecting an input signal prior to the impending event, a responsive system may be triggered to delay or to prepare for the impending event. Regardless of the specific input, the proactive sensor in these embodiments may trigger an actuator to perform an action upon the input to delay or to prepare for the occurrence of the impending event. For example, if an impending defecation or urination is to be detected via the electrical activity of the external anal sphincter muscles, the system is preferably triggered (i.e., the responsive system is activated) by a signal related to relaxation of the anal sphincter. The actuator may then perform a function such as sending an electrical signal to the external anal sphincter muscle to keep the anal sphincter closed.

The actuator 70 may be disposed in and/or operatively connected to any portion of disposable article that will allow the actuator to perform a responsive function upon the bodily waste, the wearer, the article, or a component thereof. In article 20, for example, the actuator 70 may be located in the front waist region 36, the rear waist region 38 or the crotch region 37 of article 20, and may be integral with, disposed adjacent to or joined to a component of the chassis 22, the topsheet 24, the backsheet 26, the absorbent core 28, side panels 30, leg cuffs 32, a waist feature 34, a fastening system 40, the longitudinal 50 or end 52 edges, etc. The actuator 70 may also be completely contained within the article such as article 20, may have a portion located in the article and a portion located outside the article 20, or may be completely external to the article 20. An actuator 70 or a portion of an actuator 70 may be operatively connected to one or more sensors 60, one or more controllers 80, another portion of the actuator 70 or another portion of the article 20. Further, the actuator 70 may be integral with the article 20, or may be installed by the caretaker or the wearer.

The article 20 may also include a controller 80. A "controller" is defined for the purposes of this application as a device that receives an input from a sensor and determines if one or more actions are to be taken upon the input. The controller may receive a signal from the sensor 60 and direct the actuator 70 to perform a responsive function upon the input. Alternatively, the actuator 70 may receive the signal directly from the sensor 60 and perform a responsive function upon the input. A controller may include materials that undergo chemical or physical change, may be a chemical, mechanical or electrical device that processes information from a sensor, etc. For example, in an article having a compressed plastic foam material encapsulated and restrained under vacuum by a moisture soluble bag, the sensor 60 may comprise the moisture soluble bag. The physical and chemical characteristics of the film, i.e., the type of polymer, the thickness, etc., that determine how much of the input must be present before the film will dissolve act as the controller 80 and determine the threshold level of input that must be met before the controller 80 allows the actuator 70 to release stored energy to perform a responsive function upon the input. The actuator 70 is the combination of the compressed foam and the loss of vacuum, which allows release of the stored mechanical energy of the compressed foam. In this example, the controller 80 acts as a one-time switch. An electrical controller 80 that receives signals from the sensor 60 such as electrical activity of muscles of the wearer, however, may receive and monitor multiple electrical signals and may repeatedly trigger the actuator to act upon the input. The controller may be integral with the sensor component, integral with the actuator component, or a separate component of the system.

The controller 80 may be disposed in and/or operatively connected to any portion of a disposable article that will allow the controller 80 to receive a signal from the sensor 60 and to provide a signal to the actuator 70. In article 20, for example, the controller 80 may be located in the front waist region 36, the rear waist region 38 or the crotch region 37 of article 20, and may be integral with, disposed adjacent to or joined to the chassis 22, or a component of the topsheet 24, the backsheet 26, the absorbent core 28, side panels 30, leg cuffs 32, a waist feature 34, a fastening system 40, the longitudinal 50 or end 52 edges, etc. The controller 80 may be integral with the article 20, or may be installed by the caretaker or the wearer. The controller 80 may be completely contained within the article such as article 20, may have a portion located in the article and a portion located outside the article, or may be located completely outside the article 20. A controller 80 or a portion of a controller 80 may be operatively connected to one or more sensors 60, one or more actuators 70, another portion of the controller 80 or another portion of the article 20. The controller 80, for example, may receive a signal from the sensor 60 and provide a signal to the actuator 70, e.g., by a radio frequency (rf) transmission.

Figure 5:
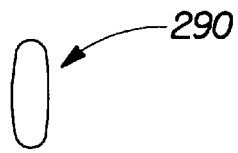
FIG. 5 shows a perspective view of an embodiment of the present invention including a soluble capsule.

Although distinct structural elements may perform the sensor 60, actuator 70 and controller 80 functions, the sensor 60, actuator 70 and/or controller 80 functions of the present invention need not be performed by distinct structural elements. The sensor 60 and controller 80 functions, for example, may be performed by the same structural element such as a film that dissolves in contact with a component of a bodily waste. In this example, the film acts as a sensor and responds to the input component of bodily waste. The physical and chemical characteristics of the film, i.e., the type of polymer, the thickness, etc., that determine how much of the input must be present before the film will dissolve act as the controller and determine the threshold level of input that must be met before the controller allows the actuator to release stored energy to perform a responsive function upon the input. In another embodiment, the responsive system may comprise cells or capsules 290 (see, e.g., FIG. 5) that contain one or more materials such as skin care compositions, pH control agents or enzyme inhibitors. The cells or capsules may, for example, dissolve in the presence of a threshold level of a given liquid or other component of bodily waste and release a stored material to act upon the input. In this embodiment, the cells or the capsules act as both the sensor, e.g., detecting the liquid, and the controller, e.g., defining the threshold level before allowing the material to be released. In yet another embodiment, the responsive system may comprise a closed system liquid transport member that may receive an input such as urine at the inlet port and discontinuously deliver an agent such as a pH control agent or an enzyme to the urine at the outlet port of the transport member. In this embodiment, the transport member both acts as the sensor, i.e., receiving urine, and the actuator, i.e., actively delivering the agent to the input to be treated. In addition, the closed system liquid transport member may further act as a controller that determines the necessary threshold level of the input. In an embodiment in which the closed system liquid transport member receives urine at the inlet port and transports the urine to another portion of the article, for example, the closed system liquid transport member may act as the sensor, the actuator and/or the controller. In this embodiment, the transport member may act as a sensor by receiving the urine, the permeability of the inlet port or the outlet port may function as the controller and determine the threshold quantity of urine that is required before the transport member functions as the actuator by transporting the urine to another portion of the article.

The article 20 of the present invention includes a responsive system including a feedback control loop, i.e., a closed loop system. A "responsive system" is defined for the purposes of this application as a system that includes a sensor 60 and an actuator 70 that acts upon the bodily waste, the wearer, the article, or a component thereof when the sensor 60 detects the appropriate triggering input. Upon sensing a given input parameter, the actuator 70 effects the release of stored energy or material to perform a responsive function upon the given input.

Figure 6A:
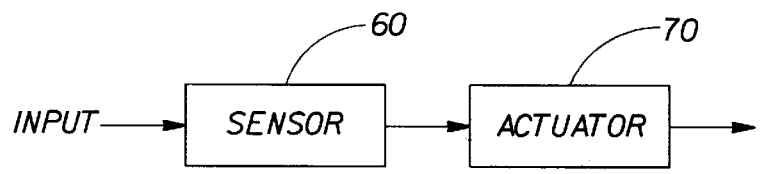
FIG. 6A shows a block diagram of an exemplary open loop responsive system.
Figure 6B:
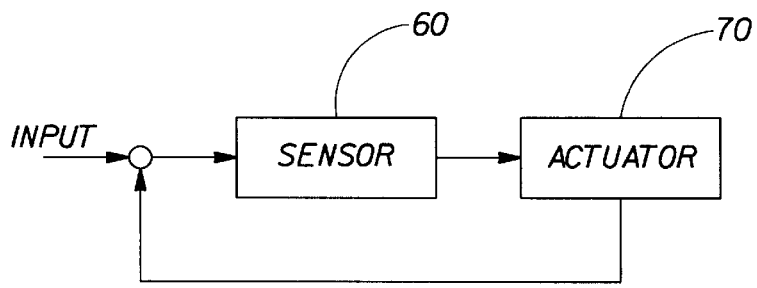
FIG. 6B shows a block diagram of an exemplary closed loop responsive system.
Figure 6C:
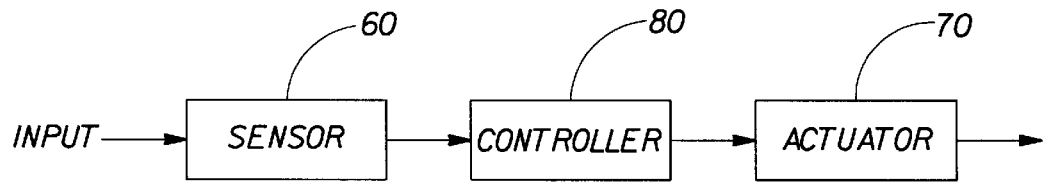
FIG. 6C shows a block diagram of an exemplary open loop responsive system including a controller.
Figure 6D:
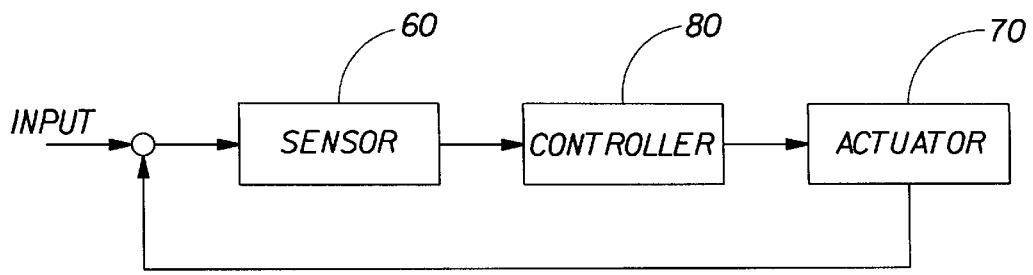
FIG. 6D shows a block diagram of an exemplary closed loop responsive system including a controller.

A responsive system of the present invention comprises a "closed loop" instead of an "open loop" system. A "closed loop" system of the present invention, which is also referred to as a "feedback control loop" system, includes distinct sensor 60 and actuator 70 components and performs a responsive function upon the input. In some preferred embodiments, the system may also use a detection or a measurement of an element or a parameter of the output condition as at least one trigger of the responsive function that is performed upon the input. The output condition may be the state of the input condition after the actuator 70 has had the opportunity to perform a responsive function on the input condition. For example, if the sensor 60 is monitoring pH in the article 20 and urine is discharged into the article 20 changing the pH of the system, i.e., the output condition of the responsive system, the responsive system may release a predetermined quantity of a pH buffer to bring the pH of the system back to the desired target pH or pH range or may release a buffer until the pH returns to the target pH or the pH range. An absorbent material such as a super absorbent polymer that continually absorbs a liquid input until the liquid has all been absorbed or the capacity of the polymer has been reached, however, is not considered to comprise a closed loop system because the absorbent material does not have distinct sensor 60 and actuator 70 components. The responsive function may be performed when the output condition reaches a threshold level, or may be performed only when the output condition and one or more other conditions are met. Acting upon the input may include acting upon the element sensed, e.g., sensing pH and acting upon the pH, or may include acting upon a composition of which the element sensed is an integral component, e.g., sensing a fecal enzyme or fecal moisture and acting upon feces. As described above, a feedback control loop system includes at least two distinct components: the sensor 60 and the actuator 70. A block diagram of an exemplary feedback control loop including a sensor 60 and an actuator 70 is shown in FIG. 6B. The sensor 60 detects an event, or a parameter associated with that event. The actuator 70 receives a signal and performs a responsive function on the input condition detected by the sensor 60. As described above, the feedback control loop may further include a controller 80. A block diagram of an exemplary feedback control loop including a sensor 60, an actuator 70 and a controller 80 is shown in FIG. 6D. In this case, the sensor 60 may provide a signal to the controller 80, and the controller 80 may direct the actuator 70 to perform a responsive function upon the input condition. The controller 80 may be a separate component of the responsive system or the controller function may be performed by the sensor 60 and/or the actuator 70.

The feedback control loop of the present invention may be "non-modulating" or "modulating." In a "non-modulating" feedback control loop responsive system the responsive system acts as a one-time switch in which the actuator performs a responsive function on the input when the threshold level of the output condition is met. For example, the sensor 60 may detect a specific fecal enzyme, and the actuator 70 may release a compressed foam in response to capture the feces or may release an enzyme inhibitor in response that acts upon the enzyme detected in the feces. Alternatively, the sensor 60 may detect urine or menses moisture and release a compressed foam or absorbent material in response that draws the moisture into the material as it expands. The sensor 60 may also detect a volatile gas that produces an offensive odor, and the actuator 70 may release a deodorant in response that eliminates the odor of that volatile gas. In each of these examples, the actuator 70 acts upon the input detected by the sensor 60. If the sensor 60 detects urine and the actuator 70 releases a compressed foam material to create a shaped void of sufficient volume to contain feces, however, the actuator 70 acts upon something other than the input detected by the sensor 60, i.e., acts upon the feces instead of the urine and is therefore not a feedback control loop. A "modulating" feedback control loop, however, includes a sensor 60, an actuator 70 and a controller 80. In a modulating feedback control loop, the output condition is monitored constantly or repeatedly, and the controller 80 directs the actuator to perform a responsive function on the input in order to maintain the output condition at a desired set point or within a desired range. A modulating responsive system may constantly or repeatedly measure pH in waste and release a given quantity of a pH control agent (such as a pH buffer or a pH decreasing agent) each time the pH of the waste is detected above a threshold pH level to provide a feedback control loop responsive system.

In contrast to a closed loop system of the present invention, an "open loop" system is a system that responds to the input to perform a responsive function without using feedback, i.e., the output has no effect upon the sensed input entering the system. A block diagram of an exemplary open loop system including a sensor 60 and an actuator 70 is shown in FIG. 6A. A block diagram of an alternative open loop system further including a controller 80 is shown in FIG. 6C. An open loop system may include a responsive system that has a single device that performs the functions of both the sensor 60 and the actuator 70 or may have distinct sensor 60 and actuator 70 components in which the actuator acts upon something other than the input. A super absorbent polymer placed in an absorbent core of a disposable absorbent article, for example, provides an open loop response because the polymer only includes a single device that performs the functions of the sensor 60 and actuator 70. Alternatively, an open loop responsive system may include a sensor 60 that detects bodily waste or a component of that bodily waste, and an actuator 70 that performs a responsive function in a continuous or a discontinuous manner on something other than the input detected by the sensor 60. For example, the sensor 60 may detect urine, and the actuator 70 may capture or store feces. One example of a continuous open loop responsive system in which an inflatable spacer inflates to provide a void volume to store feces via a stoichiometric chemical reaction when a liquid such as urine contacts a gas evolving material, i.e., a continuous responsive system, is described in U.S. Pat. No. 5,330,459 entitled "Disposable Absorbent Article Having An Inflatable Spacer," issued to Gary D. Lavon et al. on Jul. 19, 1994, which is incorporated herein by reference. Another example of an embodiment of this type is a disposable article that improves the fit on the wearer by the actuator releasing a leg cuff that has been held in an expanded state when the sensor 60 detects a liquid such as urine or menses. An example of a continuous open loop responsive system that improves the fit of the wearer via a stoichiometric chemical reaction is described in U.S. Pat. No. 4,246,900 entitled "Diaper Including Moisture-responsive Seal Means," issued to Schr öder et al. on Jan. 27, 1981, which is incorporated herein by reference. Alternatively, a discontinuous open loop responsive system that improves the fit on the wearer may include an elastic material such as a leg or waist cuff that is held in an expanded state at two distinct restraint points by a soluble restraining material such that when the restraining material at one or both of the restraining points dissolves, the elastic material may contract and form a seal with the skin of the wearer.

A closed loop responsive system of the present invention may respond in either a "continuous" or a "discontinuous" manner. As used in this application, a "continuous responsive system" refers to a responsive system in which the output is quantitatively dependent upon the quantity of the input (i.e., continuously increasing quantities of the input are required to effect continuously increasing quantities of the output), or where the output of the responsive system comprises a passive release of a stored material. A super absorbent polymer placed in an absorbent core of an article, for example, provides a continuous response in which the output is quantitatively dependent upon the quantity of the input, i.e., as increasing quantities of liquid waste contact the super absorbent polymer, an increasing amount of the polymer contains that liquid until the capacity of the polymer is exhausted. A stoichiometric chemical reaction is another example of a system having a continuous response to increasing output. In the reaction A+ excess B→C, for example, the amount of excess B converted to C is stoichiometrically and, therefore "continuously," related to the amount of A available in the system. A responsive system that passively releases a stored material, however, generally provides a continuous response regardless of how the material itself is released because the actual responsive function performed upon the bodily waste, the wearer, the article, or a component thereof is performed by the material, not by the release of the material. Thus, whether the material is released continuously in response to a given input, or released discontinuously at a single time when a threshold of a given input is detected, the responsive function performed by the released material is performed such that continuously increasing quantities of the input are required to effect continuously increasing quantities of the output until the material released is exhausted.

Figure 7A:
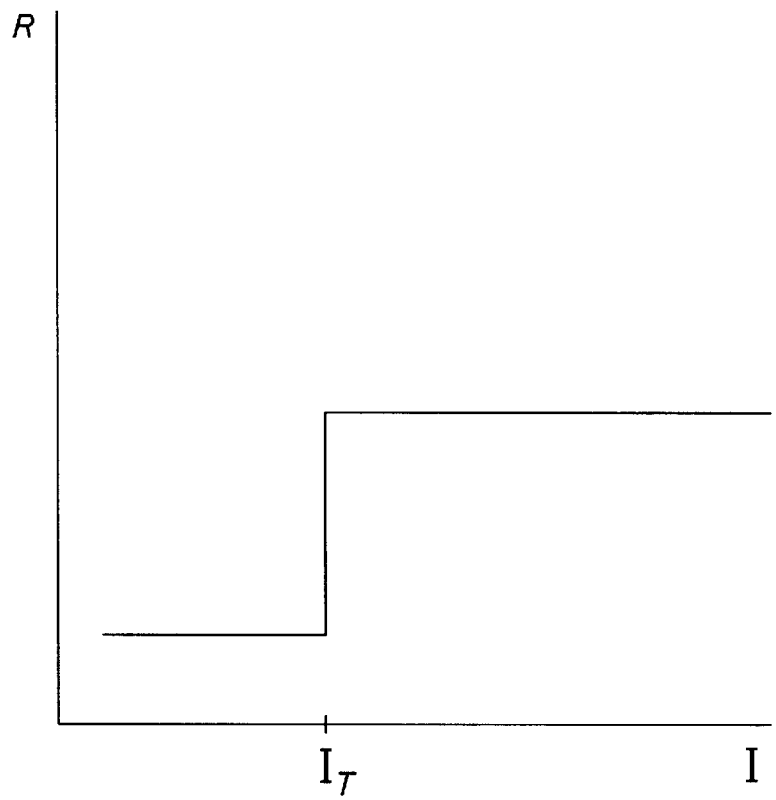
FIG. 7A shows an ideal output function of a discontinuous responsive system of the present invention having a single threshold level.

A "discontinuous responsive system," however, refers to a responsive system that has an output function that is essentially independent of the quantity of the input beyond a threshold level. For example, when one or more threshold levels of a given input are met, the responsive system may release all or a pre-designated portion of its stored energy to perform a specific responsive function. In an ideal embodiment of the present invention, the output function includes a "step" function as shown in FIG. 7A. In this embodiment, the rate of change in the output with increasing levels of input (d(output)/d(input)), i.e., the slope or first derivative f'(x) of the output function f(x), is preferably essentially zero when the amount of input is above or below the threshold level. At the threshold level, however, the d(output)/d(input) rate of change preferably approaches infinity. Thus, in the ideal discontinuous response, the limit of the function $f(x-\epsilon)$ as $\epsilon\to 0$ is not equal to the limit of the function $f(x+\epsilon)$ as $\epsilon\to 0$, i.e., $\lim_{\epsilon\to 0} f(x-\epsilon) \neq \lim_{\epsilon\to 0} f(x+\epsilon)$.

Figure 8A:
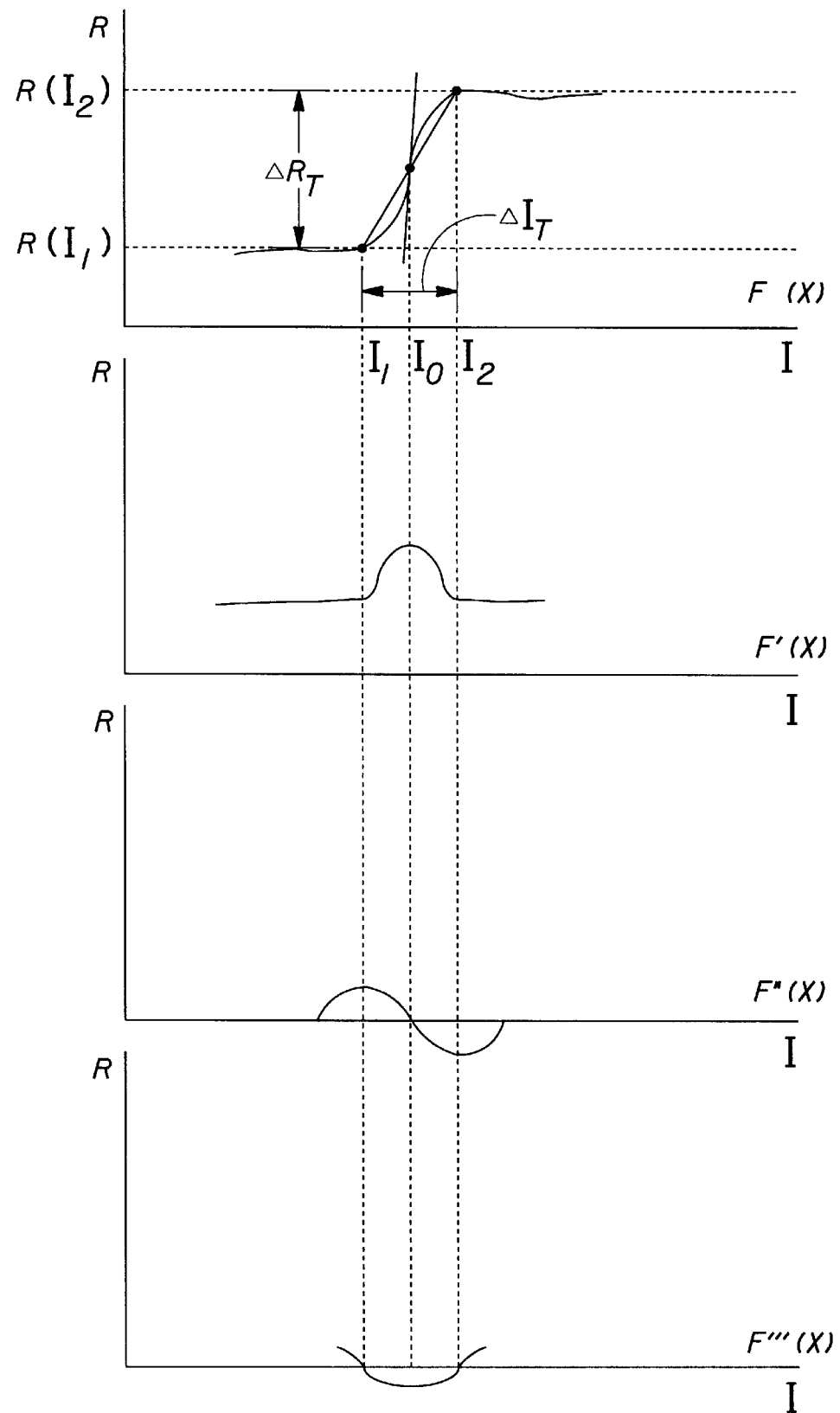
FIG. 8A shows an exemplary output function of a discontinuous responsive system of the present invention along with the first, second and third derivatives of the output function.

The present invention, however, recognizes that in the physical world an ideal instantaneous step change at the threshold level is not necessary and may not even be possible in many instances. In a preferred embodiment, it is only necessary that the output function have a virtual step change with very little change in the input at or around the threshold level of the input. Thus, the present invention contemplates a discontinuous responsive system of the present invention having an output function that responds in a sufficiently discontinuous manner in the transition region such that the output function has at least a minimum relative degree of steepness in the transition region. While not wishing to be limited to a particular method of describing or modeling a discontinuous system, in a preferred method of determining whether a given output function performs in a sufficiently discontinuous manner as defined for the purposes of the present invention, the slope of the output curve at the inflection point is compared with the relative slope of a line between the first and last points of the transition region. For example, FIG. 8A shows a graph of an exemplary output function, f(x) along with aligned graphs of the first, f'(x), second, f"(x), and third, f'"(x), derivatives of the exemplary output function. The output function f(x) describes the effect of the input (x or I) on the output or response (R(I)). For purposes of the present invention, the transition region is defined as the region between the relative maxima, $R(I_1)$, and the minima, $R(I_2)$, of the second derivative, f"(x), of the output function, f(x). The relative maxima, $R(I_1)$, and the relative minima, $R(I_2)$, are points at which the third derivative, f'"(x), equals zero. The inflection point, $I_0$, is defined as the point in the transition region at which the second derivative, f"(x), equals zero, i.e., $$\left.\frac{d^2 R}{dI^2}\right|_{I=I_0} = 0.$$

The comparison of the slope of the output function at the inflection point to the slope of a line between the first and the last points of the transition region can be described by the equation:

$$\left.\frac{dR}{dI}\right|_{I=I_0} = k \frac{(\Delta R_T)}{(\Delta I_T)}.$$

In this equation dR/dI at the inflection point is the first derivative of the output function at that point. The term $\Delta I_T$ is the change in the input to the responsive system between the first, $I_1$, and last, $I_2$, points of the transition region, i.e., $I_2-I_1$, and the term $\Delta R_T$ is the change in the response of the output function between the first and last points of the transition region, i.e., $R(I_2)-R(I_1)$. The coefficient k is a proportional constant that describes the relative steepness of the slope of the output function at the inflection point, $I_0$, compared to the slope of a line between the first and last points of the transition region. In order that the responsive system have a discontinuous output function, the proportional constant k must be at least about 2.0, preferably at least about 3.0, more preferably at least about 5.0, even more preferably at least about 10.0, with at least about 100.0 being the most preferred.

In certain embodiments, the relative degree of steepness in the transition region of a discontinuous responsive system may also be modeled by a transfer function of a control system having a series of an integer number, n, first order lags with an equal time constant. The transfer function of the responsive system is defined for the purposes of the present invention as the ratio of the Laplace transforms of the output (responding variable) to the input (disturbing variable). See, e.g., Robert H. Perry & Don Green, *Perry's Chemical*

Figure 8B:
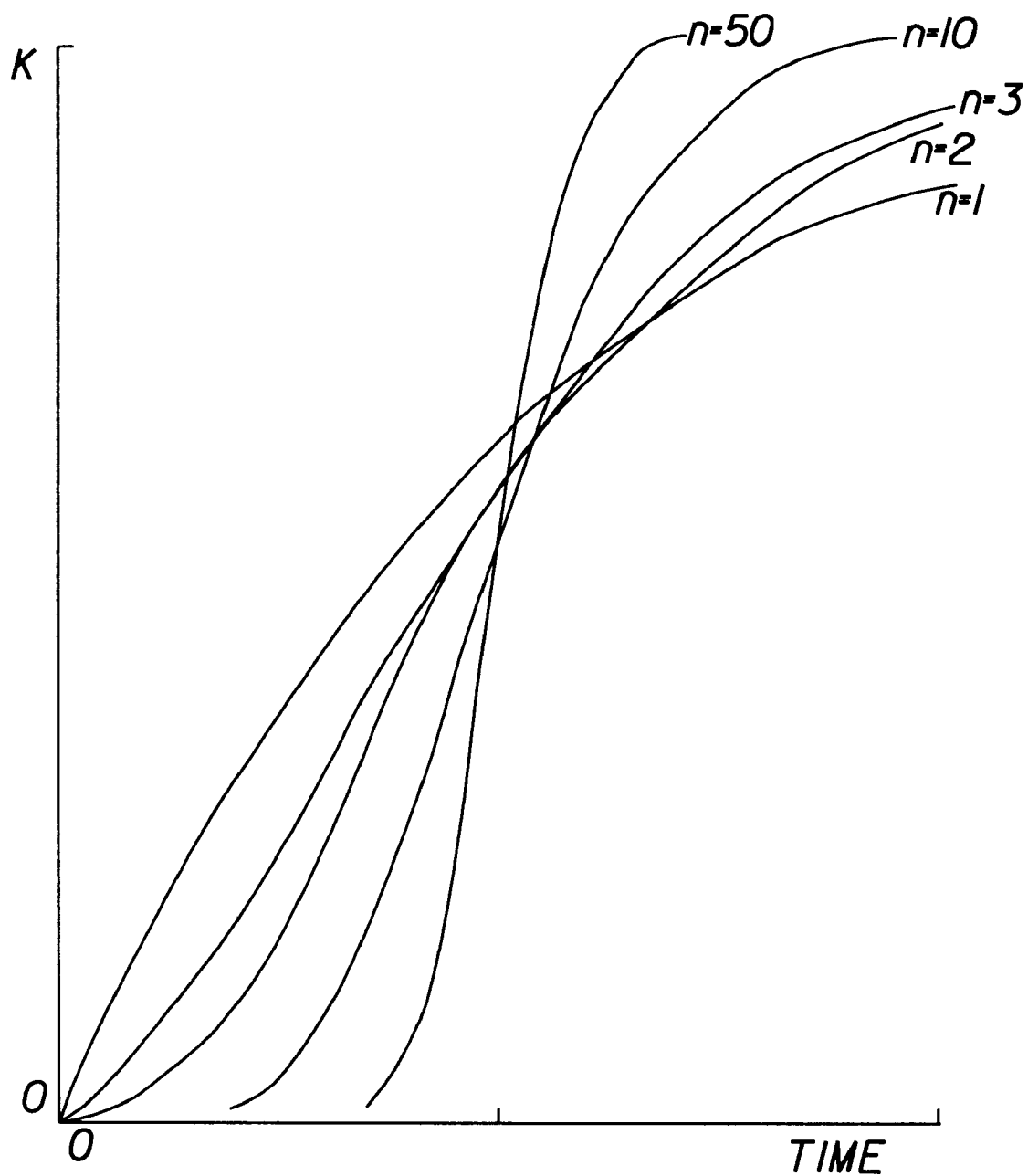
FIG. 8B shows a transfer function of a control system having a series of first order lags having an equal time constant.

*Engineers' Handbook,* Sixth Ed., Chap. 22 (McGraw Hill, Inc. 1984). As shown in FIG. 8B, the relative degree of steepness of an output function may be approximated by the formula: $KG(s)=K/(Ts+1)^n$ in which KG(s) is the transfer function, K is a proportional element, T is the time constant of the system, and n is the integer number of first order time lags. In this model, as the number n increases, the steepness of the output function in the transition region increases, and the model begins to approximate a discontinuous responsive system. Certain discontinuous responsive systems of the present invention preferably may be modeled by the above formula when n is greater than or equal to about 25, with n being greater than or equal to about 50 being more preferred, and n being greater than or equal to about 100 being the most preferred.

As shown in FIG. 7A, a responsive system of the present invention may include a single threshold level at which the responsive system may release all of its stored energy to perform a specific responsive function or may include multiple threshold levels at which the system may release a pre-designated portion of its stored energy to perform one or more specific responsive functions at each of the threshold levels. In an embodiment having a single threshold level, for example, the responsive system may release all of its stored energy to perform the entire responsive function when that threshold level is met. In such a single threshold embodiment, In this example, the discontinuous responsive system includes a system that has two states such as on or off. When a threshold quantity of an input such as bodily waste is present in the absorbent article, the responsive system may perform a single responsive function upon the waste, the wearer, the article or a component thereof, such as enveloping the waste away from the skin of the user. Thus, the discontinuous responsive system may perform a one-time "switch-like" function that changes from one state to another in the presence of a threshold level of an input.

Figure 7B:
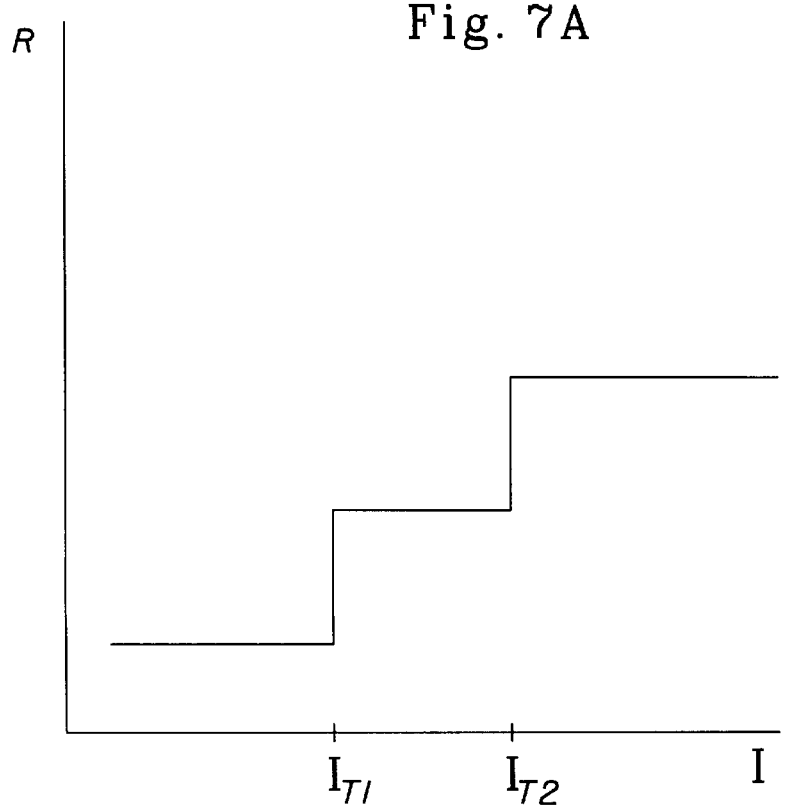
FIG. 7B shows an ideal output function of a discontinuous responsive system of the present invention having multiple threshold levels.

Alternatively, as shown in FIG. 7B, the responsive system may have multiple threshold levels such as It1 and It2 at which when each threshold level is met the system may release a given "quanta" of energy or deliver a given quantity of material to perform a specific responsive function. In this embodiment, when each threshold level is met, a portion of the entire responsive function may be performed and/or different independent responsive functions may be performed in response to different threshold levels being met. For example, a responsive system may monitor a fecal enzyme and when each threshold enzyme level is met may deliver an equal or unequal quantity of enzyme inhibitor(s), or may inflate or expand a storage component of the article or deliver a pH buffer at the first threshold level and perform another responsive function such as delivering a quantity of enzyme inhibitor(s) at the second threshold level. In each transition region, the responsive system responds essentially the same as the transition region in the single threshold embodiment described above.

In addition, a responsive system may monitor multiple inputs such as moisture and/or one or more fecal enzymes and perform one or more responsive functions when the threshold levels of the different inputs are met or may perform one responsive function only when two or more of the threshold levels of the different inputs are met. Thus, a controller may monitor multiple different inputs and perform a different responsive function when the threshold level of the different inputs are met. Alternatively, the controller may perform a logic OR-gate type function such that a responsive function may be performed when one or more threshold levels of the multiple inputs are met. The controller may also perform a logic AND-gate type function such that a responsive function may be performed when each threshold level of two or more different inputs is met.

Closed loop responsive systems of the present invention may provide a continuous or discontinuous responsive system. In one embodiment, for example, a closed loop responsive system may detect pressure and act upon the pressure such as by providing a pressure relief valve. The embodiment may comprise a continuous closed loop responsive system if the system responds continuously to pressure, increasing the output function linearly or non-linearly as the detected pressure level increases. A similar closed loop responsive system, however, may provide a discontinuous response that does not respond until the detected pressure level reaches one or more threshold levels and then releases all or a portion of its stored energy when the sensor detects that the pressure level has reached the threshold level(s).

Figure 9A:
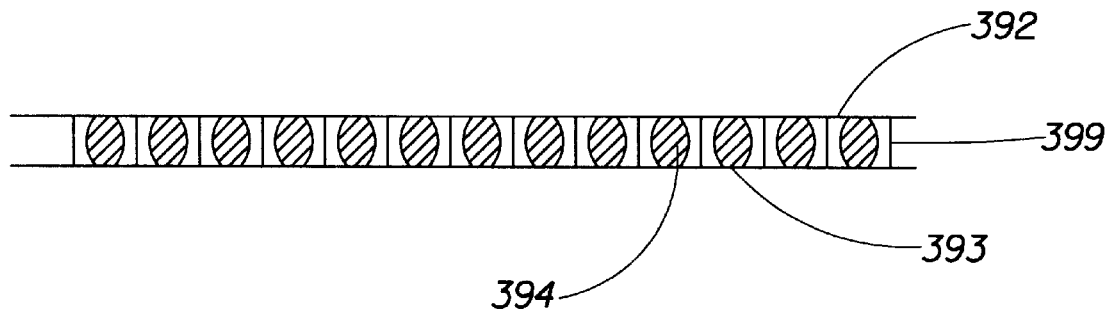
FIGS. 9A, 9B and 9C show a sectional view of an embodiment of a responsive system including a mechanical pump of the present invention.
Figure 9B:
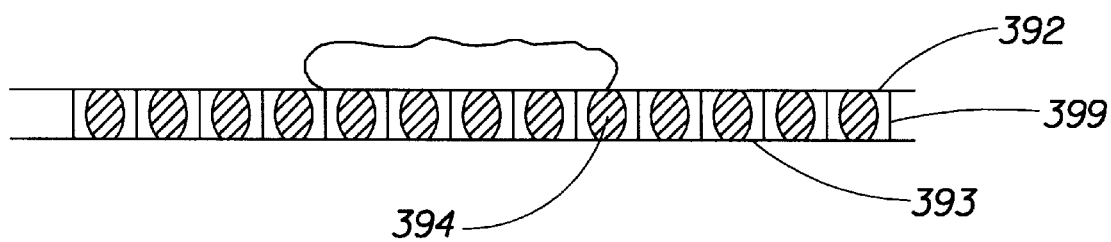
Figure 9C:
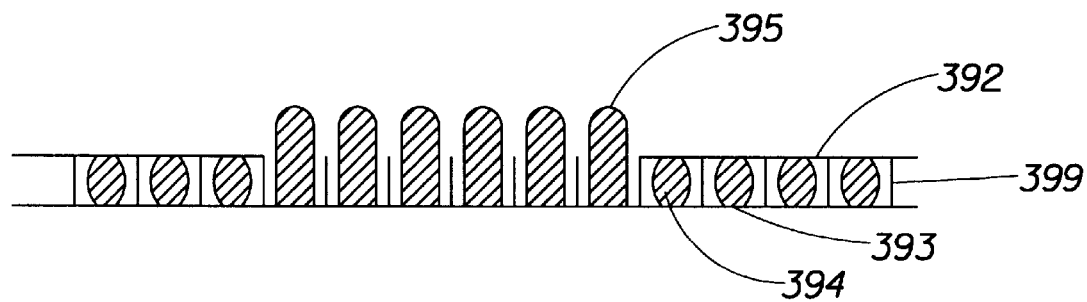

In a discontinuous embodiment of the present invention, a bodily waste isolation device 90 comprises a compressed resilient material that is held in compression within a bag, at least a portion of which is water soluble. Preferably, the compressed resilient material is held in vacuum compression within the bag. When a threshold level of moisture, i.e., the input, dissolves a portion of the water soluble region and discontinuously releases the vacuum, the compressed material expands, i.e., the increase in volume is the output, and may perform a responsive function on one or more bodily wastes. The compressed material, for example, may be a resilient plastic foam that has a shaped void that, when expanded, has a sufficient volume to capture feces. The bodily waste isolation device may be placed in the article 20 adjacent to the anus of the wearer so that when it is allowed to expand it may capture bodily wastes such as feces and store the waste away from the skin of the wearer. In a discontinuous closed loop embodiment of the present invention, the soluble bag responds to a threshold quantity of fecal moisture or fecal enzymes and the bodily waste isolation device captures feces in response. Alternatively, the compressed material may be an absorbent material that functions as a pump by drawing fluid into its body as it expands. As shown in FIGS. 9A through 9C, for example, a high porosity, large cell, resilient foam 394 as described above may be compressed and contained in a film, envelope, bag or capsule having at least a soluble portion 392 and an insoluble backing 393. FIG. 9A shows an exemplary mechanical pump of the present invention. FIG. 9B shows feces on the structure, and FIG. 9C shows the structure after the feces is absorbed. Preferably, each cell comprising the compressed foam is individually held under vacuum. When a liquid such as urine, menses or fecal moisture contacts the soluble film, the film dissolves and allows the compressed foam 394 in the cells contacted by the feces to expand 395 and draw fluid into the foam as it expands. In one embodiment, the absorbent material may include multiple cells 399 in order to maintain a suction with overlying waste. In this embodiment, if the responsive system pumps the fluid that is detected by the soluble material, the responsive system comprises a discontinuous closed loop responsive system because the system acts upon the input detected by the sensor.

Figure 2:
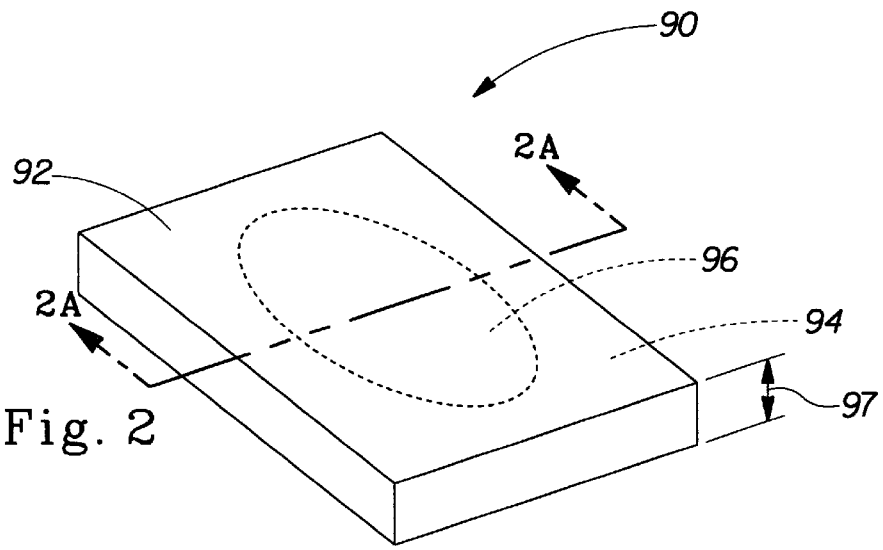
FIG. 2 shows a perspective view of a bodily waste isolation device of the present invention in a compressed state before activation.
Figure 2A:
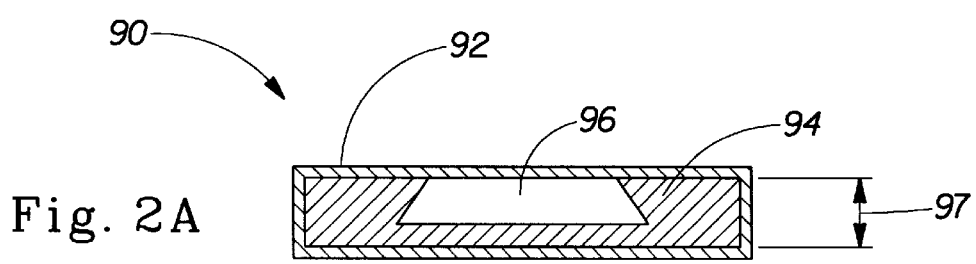
FIG. 2A shows a sectional view taken along line 2A—2A of FIG. 2.
Figure 3:
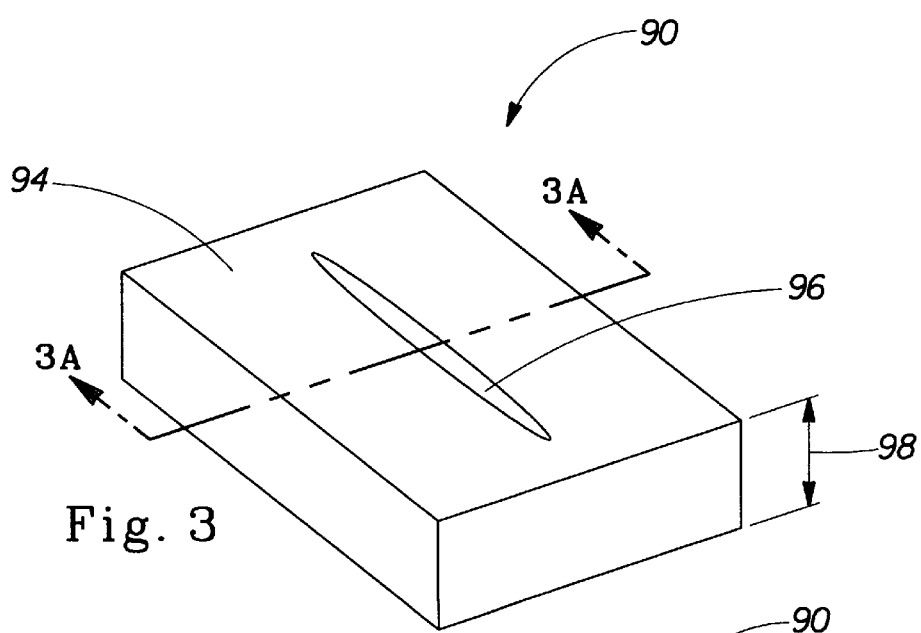
FIG. 3 shows a perspective view of one embodiment of FIG. 2 after activation.
Figure 3A:
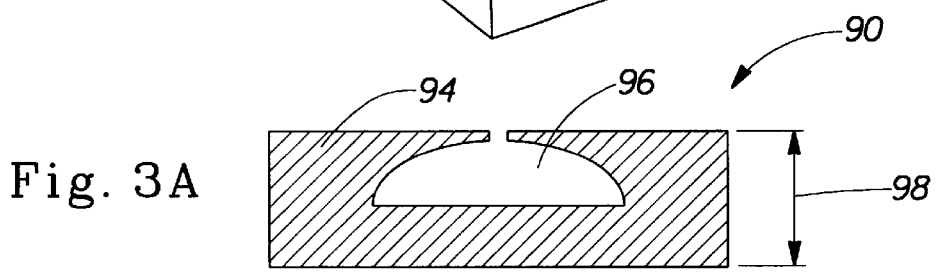
FIG. 3A shows a sectional view of FIG. 3 taken along line 3A—3A of FIG. 3.
Figure 4:
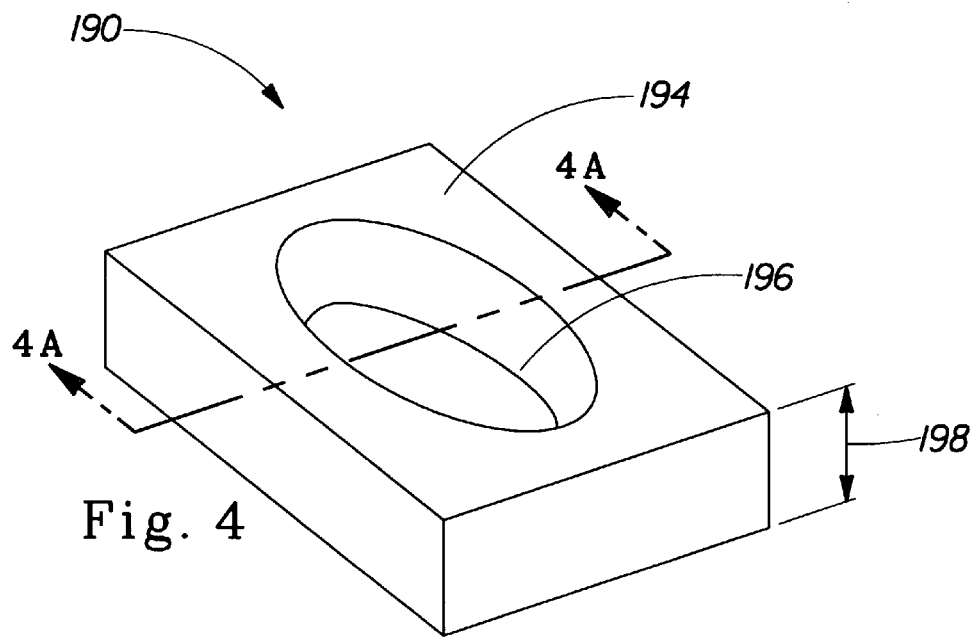
FIG. 4 shows a perspective view of an alternative embodiment of FIG. 2 after activation.
Figure 4A:
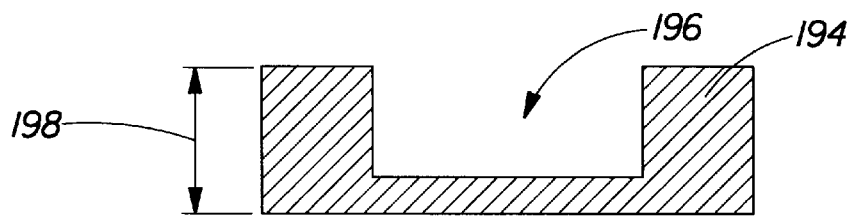
FIG. 4A shows a sectional view of FIG. 4 taken along line 4A—4A of FIG. 4.

In the bodily waste isolation device 90 embodiment shown in FIGS. 2, 2A, 3 and 3A, the compressed material 94 may comprise any elastic foam that has suitable compression and recovery properties so that it is capable of being compressed and held within the bag 92 and also capable of recovering a substantial proportion of its original height, preferably at least about 75%, after release of a constraining force. At least a portion of the bag 92 comprises a soluble region or a soluble seal. The soluble region or seal may dissolve in contact with, for example, fecal moisture, fecal enzymes, etc. The bag 92 preferably retains the compressed material 94 in a vacuum compression state until a portion of the soluble region of the bag 92 dissolves enough (i.e., a threshold level of water is detected) to discontinuously release the vacuum. Once expanded, the foam is also preferably rigid enough to withstand the weight of a baby, for example, so that the foam will not compress significantly, preferably less than about 50%, and release the captured waste if the baby sits on the device. An EVA foam, for example, such as the ones available from Foamex Corporation of Eddystone, Pa. identified as SIF/210PP1 or Aquazone 80A foam, or from Sentinel Products Corporation of Hyannis, Mass. identified as MC1900 EVA 2 lb/ft$^3$, or a foam as described in U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997 may be used as the feces capture compression material 94. As shown in FIGS. 2 and 2A, the compression material 94 may include an aperture 96 that is open when the compression material 94 is compressed. When the compression material 94 expands, the aperture 96 may be enclosed by the perimeter of the compression material 94 as shown in FIGS. 3 and 3A. This allows the waste to be captured or encapsulated away from the skin of the wearer inside the aperture 96 of the compression material 94. Alternatively, as shown in FIGS. 4 and 4A, the compression material 194 may have an open aperture 196 that acts as a spacer and provides a void space having a sufficient volume to store bodily waste deposited in the article 20. This allows the compression material 194 to receive multiple bodily waste insults after the compression material 194 has expanded.

The bag 92 may be soluble in the presence of one or more different types of input, such as water, urine, fecal enzymes, a pH level, etc., and may have physical and/or chemical characteristics (e.g., thickness) that may be designed to set a threshold level of that input required to dissolve the bag. The soluble bag 92 may, for example, comprise a plastic film that is soluble to water such as a PVA film supplied by Chris-Craft Industrial Products, Inc. of South Holland, Ill. as MONOSOL M7031 film, or H. B. Fuller Company of St. Paul, Minn. as HL 1636 or HL 1669-X. The film thickness, for example, may also be modified to provide a desired activation. The film used may, for example, also have a thickness in the range from about 0.0005 to about 0.0015 inches. An HL 1636 film having a thickness of about 0.001 inches, for example, will activate with a moisture content of about 0.049 grams per square inch.

In this embodiment, the bodily waste isolation device 90 operates as a non-modulating, discontinuous responsive system having a feedback control loop. The soluble portion of the bag 92 acts as a sensor that responds to a specific input. The sensor may, for example, be responsive to fecal moisture and/or fecal enzymes. When any soluble portion of the bag 92 contacts a threshold level of fecal moisture or a fecal enzyme, the soluble portion of the bag 92 dissolves and releases the compression material, which expands to capture, surround or envelop the feces deposited upon the article 20. The physical and chemical characteristics of the material used to form the bag 92 define the threshold level of the input and act as a controller that determines when the compression material 94 is to be released. When the bag dissolves, the release of the vacuum and the expansion of the compression material 94 function as an actuator to capture the bodily waste. Thus, the bodily waste isolation device 90 acts as a one-time discontinuous switch that releases the stored mechanical energy of the compression material 94 when a threshold level of a given input is detected. The useful energy of the responsive system includes: (stored energy)−(hysteresis loss). The compression material 94 used preferably has a minimal hysteresis loss and a maximum recovery. More preferably, the compressive hysteresis loss is less than about 25% so that the recovery upon release is at least about 75%. In this embodiment, the responsive system comprises a feedback control loop because the system uses a measure of the output, i.e., the feces present on the surface of the article and/or adjacent to the skin of the wearer, as the trigger of a function to capture or surround that feces. In this example, the feedback control loop responsive system is non-modulating because it acts as a one time switch and does not continually or repeatedly alter the input to maintain a desired set point level for the output. In contrast to the embodiment of the present invention, however, a bodily waste isolation device may comprise an open loop system if the bag 92 dissolves in urine and the device 90 captures feces, for example, the responsive system comprises an open loop system because the output of the system, i.e., the feces present on the surface of the article and/or adjacent to the skin of the wearer, does not affect the input, i.e., the urine.

A continuous closed loop embodiment of the present invention may comprise a pH sensitive, water soluble film that forms an envelope around a pH buffer system. The soluble material described above may be pH-sensitive. As such, the soluble material may have a pH threshold. The "pH threshold" of a soluble material is the pH at which the material changes from soluble to insoluble or vice-versa. For example, the soluble material may be substantially insoluble at pH of less than 6, but soluble at a pH of greater than 6. Thus, the pH threshold of that material is a pH of 6. In preferred embodiments of the present invention, the pH threshold of the soluble material is preferably between about 5 and about 9, and preferably between about 5.5 and about 8.5, although other pH thresholds are contemplated. The change in pH may be the cause or trigger for the dissolution of the soluble material, or it may also be used to help increase or decrease the rate of dissolution of the waste passage member. Thus, the performance of the waste passage member can be varied depending on factors such as the type and amount of waste deposited onto the article. A waste passage member is further described in U.S. application Ser. No. 09/106,423 (P&G Case Number 7191, entitled "Directionally Preferential Waste Passage Member For Use With Disposable Absorbent Article" filed on Jun. 29, 1998, which is incorporated by reference herein. The pH sensitive film preferably has a pH threshold in the range of about 5 to 7. The pH buffer, for example, may be a pH 7 phosphate buffer available from Corning, Inc., Corning, N.Y. (Cat #473650). When the threshold pH is reached, the pH buffer is released and functions in a continuous manner via a stoichiometric chemical reaction. The system is closed loop because the system detects pH and acts upon the pH, i.e., the input.

In another embodiment of the present invention, a foam such as described in the above example or another resilient material may be twisted creating torsional mechanical potential energy and enclosed in a soluble film envelope, bag or capsule as described above. Preferably, the twisted resilient material is held in the twisted position in the soluble film, envelope, bag or capsule under vacuum. In this embodiment, when a threshold level of moisture, pH, etc. is detected the film or capsule dissolves, discontinuously releasing the vacuum, and releasing the foam. The stored torsional mechanical potential energy causes the foam to unwind and may perform a responsive function such as storing, capturing or entrapping bodily waste such as feces, urine or menses, wiping the skin of the wearer, applying a skin treatment agent to the skin of the wearer, etc. If the soluble material dissolves in the presence of fecal moisture or a fecal enzyme, for example, the embodiment comprises a closed loop response if the responsive system performs a responsive function on the feces such as transporting the feces by a "corkscrew" pump effect. In this embodiment, the responsive system provides a non-modulating, discontinuous response. As opposed to the closed loop embodiment of the present invention, however, if the actuator acts on something other than the input such as the skin of the wearer, the responsive system comprises an open loop system.

In another embodiment, an electrical sensor may detect changes in the electrical activity of the wearer's external anal sphincter muscles to predict an imminent urination and/or defecation, i.e., a proactive sensor. Upon detection of a threshold signal drop in electrical activity of the muscles, the controller may trigger the actuator to send an electrical actuating current to the anal sphincter to close it until defecation is convenient for the wearer. In this embodiment of the present invention, the responsive system includes a feedback control loop that responds to an electrical activity in the anal sphincter muscles, and sends a signal to the anal sphincter muscles to keep the anal sphincter closed. In comparision to the embodiment of the present invention, however, the sensor or the controller may, for example, trigger the opening of a valve to release water to dissolve a water soluble portion or seal of a bag that holds a compressed foam in vacuum compression as described above, in preparation to capture waste of the imminent urination and/or defecation or effect the release of a skin care composition to treat the skin surface prior to feces contact of the skin. In these embodiments, the responsive system comprises an open loop responsive system because the system is acting upon something other than the electrical activity input signal, i.e., it is acting on the feces or the article.

In yet another embodiment, a pH control agent may be embedded in a film or granules, or held under a film of a pH-sensitive material that is insoluble, i.e., a solid, below a predefined pH (e.g., less than a pH of about 6.0), but soluble above that pH level. Upon detection of the threshold pH level or above, the pH-sensitive embedding or overlying material dissolves, releasing the pH control agent to treat the waste and/or the skin of the wearer. In the case of the embedded pH control agent, the responsive system releases the agent in a continuous manner as the embedding material dissolves. In the case of the pH control agent being held under a film, the responsive system releases the agent in a discontinuous manner after the film has dissolved. A pH control agent may be a buffer, a pH decreasing agent, e.g., an acid, or a pH increasing agent, e.g., a base. A variation of this embodiment may include a substrate that will result in a pH change upon hydrolysis by one or more target enzymes that may be present in a bodily waste such as feces, urine or menses. When the target enzyme reacts with the substrate, the reaction creates a pH change that may react with a pH sensitive material similar to the one described above to release a pH control agent. An enzyme inhibitor may also be embedded in the pH-sensitive material. Presence of the target enzyme, e.g., a fecal enzyme, may result in the conversion of the substrate and a change in pH, resulting in the dissolution of the pH-sensitive material and release of the enzyme inhibitor to treat the feces or the skin of the wearer. Exemplary pH sensitive materials are known in the art and include polyacrylamides, phthalate derivatives, formalized gelatin, shellac, keratin, cellulose derivatives, e.g., oxidized cellulose, and polyacrylic acid derivatives. Preferred materials include cellulose acetate phthalate, vinyl acetate, polyvinyl acetate phthalate, hydroxy propyl methyl cellulose phthalate and poly methacrylate blended with acrylic acid and acrylic ester copolymers. Other exemplary materials are described in EP612,520 A2 entitled "pH Triggered Osmotic Bursting Delivery Devices," which is incorporated herein by reference.

A further embodiment of a responsive system of the present invention may deliver, i.e., actively transport, an agent to an input, or a bodily waste, a wearer or an article of which the input is a component to perform a responsive function. In this embodiment, for example, the actuator 70 may comprise a compressed resilient foam or a closed system liquid transport member that delivers an agent to the input, or a bodily waste, a wearer or an article of which the input is a component when the sensor detects a the input. The agent, for example, may include a skin care composition, an enzyme inhibitor, a pH control agent. etc.

The embodiments of the present invention listed above that release or deliver pH control agents in response to the dissolving of the pH sensitive material comprise a responsive system having a feedback control loop that acts upon the pH level after a threshold pH level has been reached. These embodiments may be either modulating or non-modulating. If the pH control agent released, for example, is a buffer that contains both pH increasing and pH decreasing components, the system comprises a modulating feedback control loop system that will continually monitor the pH in the article and will maintain the pH level in the article at the desired set point or within a target range of the buffer whether the pH is raised or lowered. If the responsive system, however, releases only a pH decreasing agent at the first pH threshold level, for example, the system comprises a non-modulating feedback control loop system because the pH decreasing agent will lower the pH of the system until the agent is exhausted and will not maintain the pH of the system at a desired pH level or within a target pH range. If, however, it is known that the bodily wastes deposited in the article will raise the pH level, and the system releases a predetermined quantity of a pH decreasing agent each time the pH level in the article reaches a threshold pH level, the system may comprise a modulating feedback control loop system because it will repeatedly release the pH control agent whenever the pH of the article is above the desired set point of the system. In contrast to the embodiments of the present invention comprising a feedback control loop, however, the examples listed above that release or deliver an agent that acts upon something other than the pH level (e.g., a fecal enzyme inhibitor) in response to the pH level reaching a threshold level comprise open loop responsive systems. In these examples, the responsive system releases an agent that does not affect the input condition being monitored, i.e., the pH level.

In another embodiment, a sufficient quantity of water containing electrolytes (e.g., from urine or feces) may be detected by an electrical sensor when the electrolytic water completes a circuit, i.e., as a switch, causing current from a stored energy source such as a battery to initiate a chemical reaction such as a phase transition, etc. For example, the current may be applied to an electrically sensitive gel and cause it to change geometry and create void space for feces in the article. Again, this embodiment comprises a discontinuous responsive system that may be an open loop or a feedback control loop system depending upon whether the input sensed is being affected by the responsive system. In an embodiment of the present invention, the sensor detects fecal moisture, and the responsive system comprises a feedback control loop system because it acts upon the input being sensed. In this embodiment, the feedback control loop system may further comprise a modulating system if the void space captures the fecal moisture along with the feces, the moisture evaporates or is drawn away from the sensor element, thereby opening the circuit, and the controller activates another void space when the sensor detects fecal moisture again. In comparison, however, if the sensor detects moisture in urine, the responsive system that creates a void space for receiving feces comprises an open loop system.

In a further embodiment of the present invention, an absorbent material that swells when absorbing a liquid may be used as a sensor that, when a threshold level of swelling has occurred, mechanically closes a pair of electrical contacts in order to complete an electrical circuit. In this embodiment, the electrical circuit may trigger an actuator in a discontinuous manner to perform a responsive function on the bodily waste, the wearer, the article or any component or components thereof. For example, the actuator may open a valve to allow the liquid to flow to another portion of the article, pump the liquid to another portion of the article, initiate a change in geometry in an electrically sensitive gel to change geometry and allow the liquid to flow to another portion of the article, etc. If, however, the responsive system performs a responsive function on something other than the input such as releasing a skin care composition, etc., the responsive system would comprise an open loop system.

A material such as a fiber, film, nonwoven or other cellular structure may also be restrained in a given configuration by a material that responds to a bodily waste such as feces, or a component of that bodily waste. When the bodily waste contacts the restraining material, the restraining material may release the fiber, film, nonwoven or other cellular structure to capture or isolate the waste away from the wearer's skin. An elastic barrier, for example, may be restrained at two restraint points away from a void space in an article by a material that dissolves, weakens, etc. in response to urine, fecal moisture or a fecal enzyme. When the feces has been deposited in the void space, and the restraining material at one or both of the restraint points dissolves, the elastic barrier may contract in a discontinuous manner and cover the void space to isolate the feces from the skin of the wearer.

In another embodiment of the present invention, the responsive system may comprise a pH buffer embedded in a pH sensitive material that allows a continuous release of the pH buffer in a continuous dissolution in increased "non-target" pH water. As the moisture having a non-target pH level comes into contact with the pH sensitive material, the material dissolves in a continuous manner, and releases a quantity of the pH buffer, which changes the pH level of the moisture to the target pH level, i.e., the responsive system acts upon the input. As increasing quantities of moisture having a non-target pH level contact the pH sensitive material, the material releases an increasing quantity of the pH buffer. Therefore, the responsive system comprises a continuous closed loop responsive system.

In yet another embodiment, one or more fecal enzymes may be detected by a sensor such as an enzyme-degradable film or capsule, or a biosensor as described above to trigger a separate actuator, e.g., an electrically operated valve, to release an enzyme inhibitor to treat the skin. Exemplary enzyme inhibitors are disclosed in U.S. patent application Ser. No. 09/041,266 entitled "Disposable Absorbent Article Having A Skin Care Composition Containing An Enzyme Inhibitor" filed on Mar. 12, 1998, which is incorporated by reference herein. In yet another embodiment, certain pH conditions may be detected by the use of a pH sensitive gel, which may open a valve to release a pH control agent to treat the skin. In another embodiment, a pre-defined pressure threshold is detected, resulting in the rupture of a capsule or "bubble," effecting the release of a skin care treatment agent or composition. Exemplary skin care compositions (or lotions), are disclosed in U.S. Pat. Nos. 5,607,760 entitled "Disposable Absorbent Article Having A Lotioned Topsheet Containing An Emollient And A Polyol Polyester Immobilizing Agent," issued to Donald C. Roe on Mar. 4, 1997; 5,609,587 entitled "Diaper Having A Lotioned Topsheet Comprising A Liquid Polyol Polyester Emollient And An Immobilizing Agent," issued to Donald C. Roe on Mar. 11, 1997; 5,635,191 entitled "Diaper Having A Lotioned Topsheet Containing A Polysiloxane Emollient," issued to Donald C. Roe et al. on Jun. 3, 1997; and 5,643,588 entitled "Diaper Having A Lotioned Topsheet" issued to Donald C. Roe et al. on Jul. 1, 1997, as well as U.S. patent application Ser. Nos. 08/926,532 and 08/926,533, each filed on Sep. 10, 1997, each of the above listed patents and applications are incorporated herein by reference.

While particular non-limiting embodiments and examples of the present invention have been illustrated and described, it would be obvious to those skilled in the art that various other changes and modifications can be made without departing from the spirit and scope of the invention. For example, although the present invention is illustrated and described primarily with respect to a disposable diaper, the present invention is not limited to this embodiment. The present invention may also be used, for example, in articles that are applied directly to a wearer prior to the application of a disposable diaper or in place of a disposable diaper, in a pull-on diaper, a diaper insert, a sanitary napkin, a tampon, etc. It is therefore intended to cover in the appended claims all such changes and modifications that are within the scope of this invention.

What is claimed is:

1. A disposable article to be fitted to a wearer comprising:
   (a) a responsive system including:
      (i) a sensor operatively connected to said article, said sensor being adapted to detect an input,
      (ii) an actuator operatively connected to said sensor, said actuator being adapted to perform a responsive function upon said input, said actuator comprising a distinct component from said sensor, and
      (iii) a feedback control loop in which said actuator is adapted to perform said responsive function upon said input when said sensor detects said input.

2. The disposable article of claim 1, wherein said actuator performs said responsive function in a continuous manner.

3. The disposable article of claim 1, wherein said actuator performs said responsive function in a discontinuous manner.

4. The disposable article of claim 3, wherein said discontinuous responsive function comprises a step-type responsive function.

5. The disposable article of claim 3, wherein said discontinuous responsive function is performed such that said responsive system has an output function that may be modeled by the equation:

$$\left.\frac{dR}{dI}\right|_{I=I_0} = k\frac{(\Delta R_T)}{(\Delta I_T)},$$

wherein said constant k is greater than or equal to about 2.0.

6. The disposable article of claim 3, wherein said discontinuous responsive function is performed such that said responsive system has an output function that may be modeled by the equation:

$$\left.\frac{dR}{dI}\right|_{I=I_0} = k\frac{(\Delta R_T)}{(\Delta I_T)},$$

wherein said constant k is greater than or equal to about 3.0.

7. The disposable article of claim 3, wherein said discontinuous responsive function is performed such that said responsive system has an output function that may be modeled by the equation:

$$\left.\frac{dR}{dI}\right|_{I=I_0} = k\frac{(\Delta R_T)}{(\Delta I_T)},$$

wherein said constant k is greater than or equal to about 5.0.

8. The disposable article of claim 3, wherein said discontinuous responsive function is performed such that said responsive system has an output function that may be modeled by the equation:

$$\left.\frac{dR}{dI}\right|_{I=I_0} = k\frac{(\Delta R_T)}{(\Delta I_T)},$$

wherein said constant k is greater than or equal to about 10.0.

9. The disposable article of claim 3, wherein said discontinuous responsive function is performed such that said responsive system has an output function that may be modeled by the equation:

$$\left.\frac{dR}{dI}\right|_{I=I_0} = k\frac{(\Delta R_T)}{(\Delta I_T)},$$

wherein said constant k is greater than or equal to about 100.

10. The disposable article of claim 3, wherein said discontinuous responsive function is performed such that said responsive system has an output function that may be modeled by a control system having a transfer function of the equation: $KG(s)=K/(Ts+1)^n$, wherein said n value is greater than or equal to a value of about 25.

11. The disposable article of claim 3, wherein said discontinuous responsive function is performed such that said responsive system has an output function that may be modeled by a control system having a transfer function of the equation: $KG(s)=K/(Ts+1)^n$, wherein said n value is greater than or equal to a value of about 50.

12. The disposable article of claim 3, wherein said discontinuous responsive function is performed such that said responsive system has an output function that may be modeled by a control system having a transfer function of the equation: $KG(s)=K/(Ts+1)^n$, wherein said n value is greater than or equal to a value of about 100.

13. The disposable article of claim 1 further comprising a liquid permeable topsheet; a backsheet joined with said topsheet; and an absorbent core disposed between at least a portion of said topsheet and said backsheet.

14. The disposable article of claim 1 further comprising a controller, said controller being adapted to receive a signal from said sensor and allow said actuator to perform said responsive function when said sensor detects said input.

15. The disposable article of claim 14, wherein said controller is a distinct component from said sensor and said actuator.

16. The disposable article of claim 1, wherein said feedback control loop is selected from the group consisting of a modulating feedback control loop and a non-modulating feedback control loop.

17. The disposable article of claim 1 further comprising a second sensor, said second sensor is adapted to detect a second input.

18. The disposable article of claim 17, wherein said actuator is adapted to perform said responsive function when said sensor detects said input or said second sensor detects said second input.

19. The disposable article of claim 17, wherein said actuator is adapted to perform said responsive function when said sensor detects said input and said second sensor detects said second input.

20. The disposable article of claim 1, wherein said responsive function comprises one or more of the group selected from transforming potential energy into kinetic energy, releasing a stored material, releasing a pH control agent, releasing an enzyme inhibitor, releasing a skin care composition, delivering a stored material, delivering an active ingredient, delivering a stored material to the skin of a wearer, delivering a stored material to a bodily waste, entrapping feces, encapsulating feces, providing a void space, and pumping a liquid bodily waste.

21. The disposable article of claim 1, wherein said actuator is adapted to transform a potential energy in order to perform said responsive function, said potential energy being selected from one or more of the group of stored mechanical energy, compressive mechanical energy, torsional mechanical energy, stored chemical energy, stored electrical energy, and a battery.

22. The disposable article of claim 1, wherein said sensor is selected from the group of an electrical sensor, a mechanical sensor, a chemical sensor, and a closed system liquid transport member.

23. The disposable article of claim 1, wherein said actuator is selected from the group of release of a vacuum, a chemical actuator, an electrical pump, a mechanical actuator, a compressed resilient material, a compressed resilient material contrained in a vacuum sealed water soluble fiber, a mechanical pump, an electrical actuator, an electrically sensitive gel, a pH sensitive gel, a salt concentration sensitive gel, and a closed system liquid transport member.

24. The disposable article of claim 1, wherein said input is selected from the group of pressure, water, pH, electrical activity and an enzyme.

25. The disposable article of claim 1, wherein said article is selected from the group of: a diaper, a training pant, a sanitary napkin, a tampon, and a colostomy type bag.

26. A disposable article to be fitted to a wearer comprising:
(a) a responsive system including:
(i) a sensor operatively connected to said article, said sensor being adapted to detect an input associated with feces,
(ii) an actuator operatively connected to said sensor, said actuator including a compressed resilient material constrained in a vacuum sealed film, said actuator being adapted to encapsulate feces, and
(iii) a feedback control loop in which said actuator is adapted to encapsulate feces when said sensor detects feces.

27. A disposable article to be fitted to a wearer comprising:
   (a) a responsive system including:
      (i) a sensor operatively connected to said article, said sensor being adapted to detect an input associated with a bodily waste;
      (ii) an actuator operatively connected to said sensor, said actuator including a compressed resilient material constrained in a vacuum sealed film; and
      (iii) a feedback control loop in which said actuator is adapted to absorb said bodily waste when said sensor detects said bodily waste.

28. The disposable article of claim 27, wherein said actuator comprises a plurality of individually vacuum sealed cells.

29. A disposable article to be fitted to a wearer comprising:
   (a) a responsive system including:
      (i) a sensor operatively connected to said article, said sensor comprising a pH sensitive film,
      (ii) an actuator operatively connected to said sensor, said actuator including a pH control agent, and
      (iii) a feedback control loop in which said actuator is released when said sensor detects a pH level outside a target range.

* * * * *